United States Patent
Kraus et al.

(10) Patent No.: US 12,129,488 B2
(45) Date of Patent: Oct. 29, 2024

(54) PRODUCTION OF BROWN ADIPOCYTES

(71) Applicant: SOCIETE DES PRODUITS NESTLE S.A., Vevey (CH)

(72) Inventors: Marine Kraus, Vuarrens (CH); Stephen Dalton, Athens, GA (US); John W. Avery, III, Snellville, GA (US)

(73) Assignee: Societe des Produits Nestle S.A., Vevey (CH)

( * ) Notice: Subject to any disclaimer, the term of this patent is extended or adjusted under 35 U.S.C. 154(b) by 1065 days.

(21) Appl. No.: 17/044,085

(22) PCT Filed: Apr. 16, 2019

(86) PCT No.: PCT/EP2019/059724
§ 371 (c)(1),
(2) Date: Sep. 30, 2020

(87) PCT Pub. No.: WO2019/228705
PCT Pub. Date: Dec. 5, 2019

(65) Prior Publication Data
US 2021/0139853 A1    May 13, 2021

(30) Foreign Application Priority Data
May 28, 2018  (EP) .................................. 18174484

(51) Int. Cl.
*C12N 5/071*   (2010.01)
*A61K 35/35*   (2015.01)
*A61P 3/10*    (2006.01)
*C12N 5/077*   (2010.01)

(52) U.S. Cl.
CPC .............. *C12N 5/0653* (2013.01); *A61P 3/10* (2018.01); *C12N 2501/999* (2013.01)

(58) Field of Classification Search
None
See application file for complete search history.

(56) References Cited

U.S. PATENT DOCUMENTS

2020/0362309 A1 * 11/2020 Hafner ................. C12N 5/0653

FOREIGN PATENT DOCUMENTS

| WO | 2017009263 | 1/2017 |
| WO | 2017069222 | 4/2017 |
| WO | 2017223457 | 12/2017 |

OTHER PUBLICATIONS

Ahfeldt et al, Programming human pluripotent stem cells into white and brown adipocytes, Nat Cell Biol. 2012: 209-219.*
Zhu et al, Progress and obstacles in transplantation of brown adipose tissue or engineered cells with thermogenic potential, Frontiers in Endocrinology, 2023, pp. 1-10.*
Hafner et al, Human induced pluripotent stem cells: A new source for brown and white adipocytes, World J Stem Cells Sep. 2, 20146; 6(4): 467-472.*
Lee, M.-J., Transforming growth factor beta superfamily regulation of adipose tissue biology in obesityBBA—Molecular Basis of Disease 1864 (2018) 1160-1171.*

(Continued)

*Primary Examiner* — Maria Marvich
(74) *Attorney, Agent, or Firm* — K&L Gates LLP

(57) ABSTRACT

Use of a transforming growth factor beta (TGF-β) signalling inhibitor for producing a population of brown adipocytes in vitro.

10 Claims, 10 Drawing Sheets

Specification includes a Sequence Listing.

(56) References Cited

OTHER PUBLICATIONS

Brown AC, Brown adipocytes from induced pluripotent stem cells—how far have we come? Ann N Y Acad Sci. Mar. 2020 ; 1463(1): 9-22.*

Su et al., A Renewable Source of Human Beige Adipocytes for Development of Therapies to Treat Metabolic Syndrome, 2018, Cell Reports 25, 3215-3228.*

Chen et al. "miR-155 regulates differentiation of brown and beige adipocytes via a bistable circuit" Nature Communications, Apr. 23, 2013, vol. 4, No. 1.

Takeda et al. "Direct conversion of human fibroblasts to brown adipocytes by small chemical compounds" Scientific Rep;orts, Jun. 27, 2017, vol. 7, No. 1.

Hafner et al. "Brown-like adipose progenitors derived from human induced pluripotent stem cells: Identification of critical pathways governing their adipogenic capacity" Scientific Reports, Aug. 31, 2016, vol. 6, No. 1.

Zamani et al. "Emerging Roles fo the Transforming Growth Factor-ß Superfamily in Regulating Adiposity and Energy Expenditure" Endocrine Reviews, Jun. 2011, vol. 32, No. 3, pp. 387-403.

* cited by examiner

SEQUENCE LISTING

<160> NUMBER OF SEQ ID NOS: 1

<210> SEQ ID NO 1
<211> LENGTH: 307
<212> TYPE: PRT
<213> ORGANISM: Homo sapiens

<400> SEQUENCE: 1

Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
        35                  40                  45

Thr Ser Ser Val Ile Arg Tyr Lys Gly Val Leu Gly Thr Ile Thr Ala
    50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
                85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Val Lys Val Arg Leu Gln Ala Gln
130                 135                 140

Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190

Val Thr Tyr Asp Leu Met Lys Glu Ala Phe Val Lys Asn Asn Ile Leu
        195                 200                 205

Ala Asp Asp Val Pro Cys His Leu Val Ser Ala Leu Ile Ala Gly Phe
    210                 215                 220

Cys Ala Thr Ala Met Ser Ser Pro Val Asp Val Val Lys Thr Arg Phe
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Lys Gly Leu Val
            260                 265                 270

Pro Ser Phe Leu Arg Leu Gly Ser Trp Asn Val Ile Met Phe Val Cys
        275                 280                 285

Phe Glu Gln Leu Lys Arg Glu Leu Ser Lys Ser Arg Gln Thr Met Asp
    290                 295                 300

Cys Ala Thr
305

PRODUCTION OF BROWN ADIPOCYTES

CROSS REFERENCE TO RELATED APPLICATIONS

The present application is a National Stage of International Application No. PCT/EP2019/059724, filed on Apr. 16, 2019, which claims priority to European Patent Application No. 18174484.8, filed on May 28, 2018, the entire contents of which are being incorporated herein by reference.

FIELD OF THE INVENTION

The present invention relates to the production of brown adipocytes. More specifically, the invention relates to improved methods for differentiating cells, such as human pluripotent stem cells, to brown adipocytes.

BACKGROUND TO THE INVENTION

Diabetes mellitus (commonly referred to as diabetes) is a group of metabolic diseases that are characterised by high patient blood sugar levels over a prolonged period. The global prevalence of diabetes has reached 387 million and is projected to rise to 435 million by 2030. Indeed, 65% of the global population lives in countries where obesity contributes to more deaths than under-nutrition (WHO-2010).

There are two main types of diabetes (type 1 and type 2), which have different causes and methods of treatment. Type 1 diabetes results from the destruction of the insulin-producing beta cells in the pancreas, commonly through auto-immune mechanisms. Type 2 diabetes results from insulin resistance in peripheral tissues, which may be combined with pancreatic beta cell dysfunction, excessive body weight, poor physical activity and genetic components. About 10% of diabetes cases correspond to type 1. However, the majority of patients (85-90%) exhibit type 2 diabetes. The estimated total economic cost of diagnosed diabetes in 2012 in the US has increased by 41% compared to the previous estimate from 2007 and has reached $245 billion. This highlights the substantial burden that diabetes imposes on society.

Management of type 1 diabetes requires regular insulin injections for the lifetime of the patient. In contrast, type 2 diabetes may be controlled by management of diet, weight and physical exercise, however long-term treatment may require medication (e.g. metformin or sulphonylureas), potentially combined with insulin injections.

Although patients may be able to manage both type 1 and type 2 diabetes with existing treatments, there are currently no cures and diabetes leads to a significantly increased risk of mortality.

Energy balance to prevent the development of obesity is dependent on energy expenditure. Although physical activity is the dominant mechanism for dissipating excess energy, energy may also be dissipated through the system of thermogenesis that evolved to protect the body from hypothermia. This is based on the uncoupling of oxidative phosphorylation in brown adipocytes by the mitochondrial uncoupling protein (UCP1). Brown adipose tissue (BAT) is a highly metabolic organ that mediates energy dissipation and glucose disposal, and thus contributes to maintain an adequate energy balance and carbohydrate homeostasis.

It has been shown that up-regulation of UCP1 by genetic manipulation or pharmacological agents can reduce obesity and improve insulin sensitivity. Conversely, there is evidence in rodents that BAT dysfunction promotes obesity and impairs carbohydrate metabolism, ultimately resulting in increased functional demand on beta cells. Since the discovery of functional BAT in adult humans, inverse correlations between ageing, type 2 diabetes and the amount and activity of the BAT-depots have been reported. Upon activation, BAT converts the energy of free fatty acids and glucose oxidation into heat through UCP1. BAT has recently been demonstrated to increase triglyceride uptake and insulin sensitivity.

Studies on the characteristics and function of human brown adipose tissue has been hampered by access to the brown adipocytes themselves.

In the past, a number of techniques have been used to develop models of brown adipocytes derived from either human embryonic stem cells or mesenchymal stem cells as well as human induced pluripotent stem cells. One such protocol applied genetic engineering to force the expression of specific brown transcription factors, such as PPARg and PGC1a (Ahfeldt, T. et al. (2012) Nat. Cell Biol. 14: 209-219). However, such techniques have the disadvantage that they may generate genetic alterations that could potentially affect the function of the generated brown adipocytes. An alternative approach used a cytokine cocktail to force the differentiation of hiPSCs towards brown adipocyte-like cells (Nishio, M. (2012) Cell Metab. 16: 394-406). However, this approach appeared to be not sufficiently specific nor robust and therefore cannot be used to generate a source of human brown adipose tissue.

Accordingly, there remains a significant need in the art that provides access to brown adipocytes in order to be able to reliably study these cells in the laboratory, but also to enable further applications with these cells, such as transplantations for medical and cosmetic purposes (e.g. reconstructive or cosmetic plastic surgery).

SUMMARY OF THE INVENTION

The present inventors have developed a protocol that recapitulates developmental pathways for the directed and targeted differentiation of brown adipose cells, which uses specific growth factors in a controlled manner.

Through applying their protocol, the inventors have been able to access a highly-enriched population of human brown adipose cells with high efficiency (e.g. 80%).

Accordingly, one aspect the invention provides the use of a transforming growth factor beta (TGF-β) inhibitor for producing a population of brown adipocytes in vitro.

In one embodiment, the TGF-β inhibitor is a SMAD2 and SMAD3 inhibitor. In one embodiment, the TGF-β inhibitor is an Activin A inhibitor.

In one embodiment, the TGF-β inhibitor is:

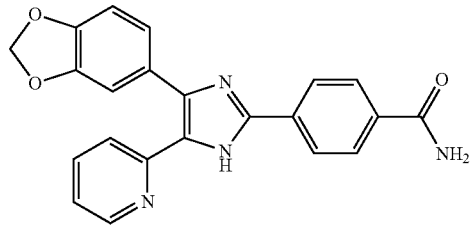 [SMILES: NC(=O)c1ccc(-c2nc(-c3ccc4c(c3)OCO4)c(-c3ccccn3)[nH]2)cc1]

or a salt or derivative thereof.

In one embodiment, the population of brown adipocytes is produced in vitro from a population of stem cells and/or a population of mesoderm cells. In a preferred embodiment, the stem cells are induced pluripotent stem cells. In a preferred embodiment, the mesoderm cells are paraxial mesoderm cells.

In one embodiment, the population of brown adipocytes is produced in vitro from a population of cells that express any one of: FOXC1, FOXC2, MRF4, MSGN1, MYF5, PAX3, PAX7, PRRX1, SIX1 and/or TBX6.

In a preferred embodiment, the population of brown adipocytes express any one of FOXC1, FOXC2, MRF4, MSGN1, MYF5, PAX3, PAX7, PRRX1, SIX1 and/or TBX6, at least by day 6 of differentiation.

In one embodiment, the brown adipocytes express UCP1 and desirably PGC1-α, PPARγ, ADIPOQ, PRDM16, ENDRB, CIDEA, D102, and/or EBF2.

In a preferred embodiment, the brown adipocytes express UCP1. In another preferred embodiment, forskolin may be added to the brown adipocytes to increase expression of UCP1.

In yet another preferred embodiment, the population of brown adipocytes express any one of these markers: UCP1, PGC1-α, PPARγ, ADIPOQ, PRDM16, ENDRB, CIDEA, D102, and/or EBF2.

In one embodiment, the population of brown adipocytes express any one of these markers: UCP1, PGC1-α, PPARγ, ADIPOQ, PRDM16, ENDRB, CIDEA, D102, and/or EBF2 at least by day 36 of differentiation.

In one embodiment, at least 70%, 80%, 90%, 95%, 96%, 97%, 98%, 99% or 100% of the population of cells express UCP1.

In another embodiment, the brown adipocytes exhibit greater uncoupled respiration and/or maximal respiration compared to white adipocytes and/or paraxial mesoderm cells.

In another embodiment, the brown adipocytes exhibit greater uncoupled respiration and/or maximal respiration when stimulated with forskolin.

In one embodiment, the brown adipocytes contain 2 or more lipid droplets, for example at least 3, 4, 5, 10, 15, 20 or 25 lipid droplets.

In another aspect, the invention provides a method for producing a population of brown adipocytes comprising the step of contacting a population of cells with a transforming growth factor beta (TGF-β) inhibitor.

In one embodiment, the method is an in vitro method.

In one embodiment, the TGF-β inhibitor is a SMAD2 and SMAD3 inhibitor. In one embodiment, the TGF-β signaling inhibitor is an activin A signaling inhibitor.

In one embodiment, the TGF-β inhibitor is:

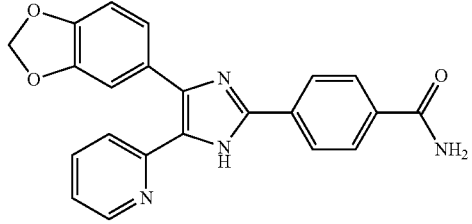 [SMILES: NC(=O)c1ccc(-c2nc(-c3ccc4c(c3)OCO4)c(-c3ccccn3)[nH]2)cc1]

or a salt or derivative thereof.

In one embodiment, the population of cells contacted with the TGF-β signalling inhibitor is a population of mesoderm cells. In a preferred embodiment, the mesoderm cells are paraxial mesoderm cells.

In one embodiment, the population of cells contacted with the TGF-β signalling inhibitor is a population of cells that express any one of: FOXC1, FOXC2, MRF4, MSGN1, MYF5, PAX3, PAX7, PRRX1, SIX1 and/or TBX6. In a preferred embodiment, the population of brown adipocytes express any one of FOXC1, FOXC2, MRF4, MSGN1, MYF5, PAX3, PAX7, PRRX1, SIX1 and/or TBX6, at least by day 6 of differentiation.

In one embodiment, the population of cells contacted with the TGF-β signalling inhibitor is produced, preferably in vitro, from a population of stem cells. In a preferred embodiment, the population of cells contacted with the TGF-β signalling inhibitor are produced using 3D cell culture. In a preferred embodiment, the stem cells are induced pluripotent stem cells.

In one embodiment, a UCP-1 activator is added to increase expression of UCP-1, a marker of brown adipocytes.

In one embodiment, the UCP-1 activator is forskolin (FSK):

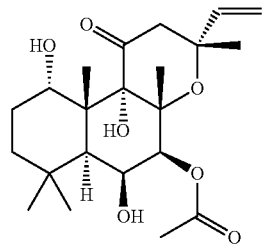

or a salt or derivative thereof.

In one embodiment forskolin (FSK) is added to stimulate the cells to increase UCP1 expression and to assess the function of the cells. In a preferred embodiment, 1-50 μM forskolin (FSK) is added for 1 to 24 hours.

In a preferred embodiment, the method comprises the steps:
(a) culturing a population of cells, preferably a population of mesoderm cells, for a first period of time in the presence of the TGF-β signalling inhibitor; and
(b) culturing the population of cells provided by step (a) for a second period of time in the absence of the TGF-β signalling inhibitor.

In one embodiment, the first period of time is about 1-15, 2-15, 3-15, 4-15, 5-15, 6-15, 7-15, 8-15, 1-14, 2-14, 3-14, 4-14, 5-14, 6-14, 7-14, 8-14, 1-13, 2-13, 3-13, 4-13, 5-13, 6-13, 7-13, 8-13, 1-12, 2-12, 3-12, 4-12, 5-12, 6-12, 7-12, 8-12, 1-11, 2-11, 3-11, 4-11, 5-11, 6-11, 7-11, 8-11, 1-10, 2-10, 3-10, 4-10, 5-10, 6-10, 7-10 or 8-10 days, preferably about 6-10 days.

In one embodiment, the second period of time is about 15-30, 16-30, 17-30, 18-30, 19-30, 20-30, 15-29, 16-29, 17-29, 18-29, 19-29, 20-29, 15-28, 16-28, 17-28, 18-28, 19-28, 20-28, 15-27, 16-27, 17-27, 18-27, 19-27, 20-27, 15-26, 16-26, 17-26, 18-26, 19-26, 20-26, 15-25, 16-25, 17-25, 18-25, 19-25, 20-25, 15-24, 16-24, 17-24, 18-24, 19-24 or 20-24 days, preferably about 15-30 days.

In a particularly preferred embodiment, the method comprises the steps:
(a) culturing a population of cells, preferably a population of mesoderm cells, for about 1-15 days, preferably about 6-10 days, in the presence of the TGF-β signalling inhibitor; and (b) culturing the population of cells provided by step (a) for about 20-50 days, preferably about 15-30 days, in the absence of the TGF-β signalling inhibitor.

In a particularly preferred embodiment, the method comprises the steps:

(a) culturing a population of cells, preferably a population of mesoderm cells, for about 1-15 days, preferably about 6-10 days, in the presence of the TGF-β signalling inhibitor; and (b) culturing the population of cells provided by step (a) for about 20-50 days, preferably about 15-30 days, in the absence of the TGF-β signalling inhibitor.

In one embodiment, the cultures of steps (a) and (b) are adherent cultures.

In one embodiment, the method comprises the further step of:

(c) culturing the population of cells provided by step (b) under conditions suitable for the formation of aggregated brown adipocytes, preferably wherein the culture is a rotational suspension culture.

Preferably the cells of the invention are mammalian cells, preferably human cells.

In another aspect, the invention provides a method of analysing brown adipocytes comprising the steps:

(a) providing a population of brown adipocytes using the method of the invention; and (b) analysing the population of brown adipocytes in vitro or implanting the population of brown adipocytes into an animal model.

In another aspect, the invention provides a population of brown adipocytes obtainable in vitro using a transforming growth factor beta (TGF-β) signalling inhibitor.

In another aspect, the invention provides a population of brown adipocytes produced by the method of the invention.

In another aspect, the invention provides a population of brown adipocytes for use in surgery and/or therapy, wherein the population of brown adipocytes is produced by the method of the invention.

In one embodiment, the use is in the treatment or prevention of diabetes.

In another aspect, the invention provides use of the population of brown adipocytes of the invention for the manufacture of a medicament for the treatment or prevention of diabetes.

In another aspect, the invention provides a method of implanting brown adipocytes into a subject comprising the steps:

(a) providing a population of brown adipocytes using the method of the invention; and (b) implanting the population of brown adipocytes into the subject.

In one embodiment, the method is a method of cosmetic surgery.

In another embodiment, the method is a method of reconstructive plastic surgery.

In another aspect, the invention provides the use of a population of brown adipocytes of the invention for the production of adipokines or secreted factors. Preferably the production is in vitro.

In another aspect, the invention provides a method of treating or preventing diabetes comprising the step of implanting the population of brown adipocytes of the invention into a subject in need thereof.

In another aspect, the invention provides a method of screening for a therapeutic agent comprising the step of contacting the population of brown adipocytes of the invention with a candidate agent. Preferably, the candidate agent is comprised within a library of candidate agents. The method of screening may, for example, be carried out in vitro or in vivo (e.g. using model animals which have been implanted with the population of brown adipocytes of the invention). Preferably, the method of screening is carried out in vitro.

Proceeding from monolayer of pluripotent stem cells (PSC) to spherical culture (Sph) to primitive streak (PS) to paraxial mesoderm (PM). Cells are then dissociated and cultured in 2D in specific BAD1 medium that contains TGFβ signalling inhibitor, SB431542 which is an activin inhibitor. SB431542 inclusion at this stage reduces appearance of vascular endothelium and cardiac myocyte development from contaminating lateral plate mesoderm. In a second step, cells are cultured in BAD2 medium allowing TGFβ signalling to be active as SB431542 is removed. Continued use of SB431542 retards proper kinetics and perturbs proper UCP1 induction and expression.

Figure 1:
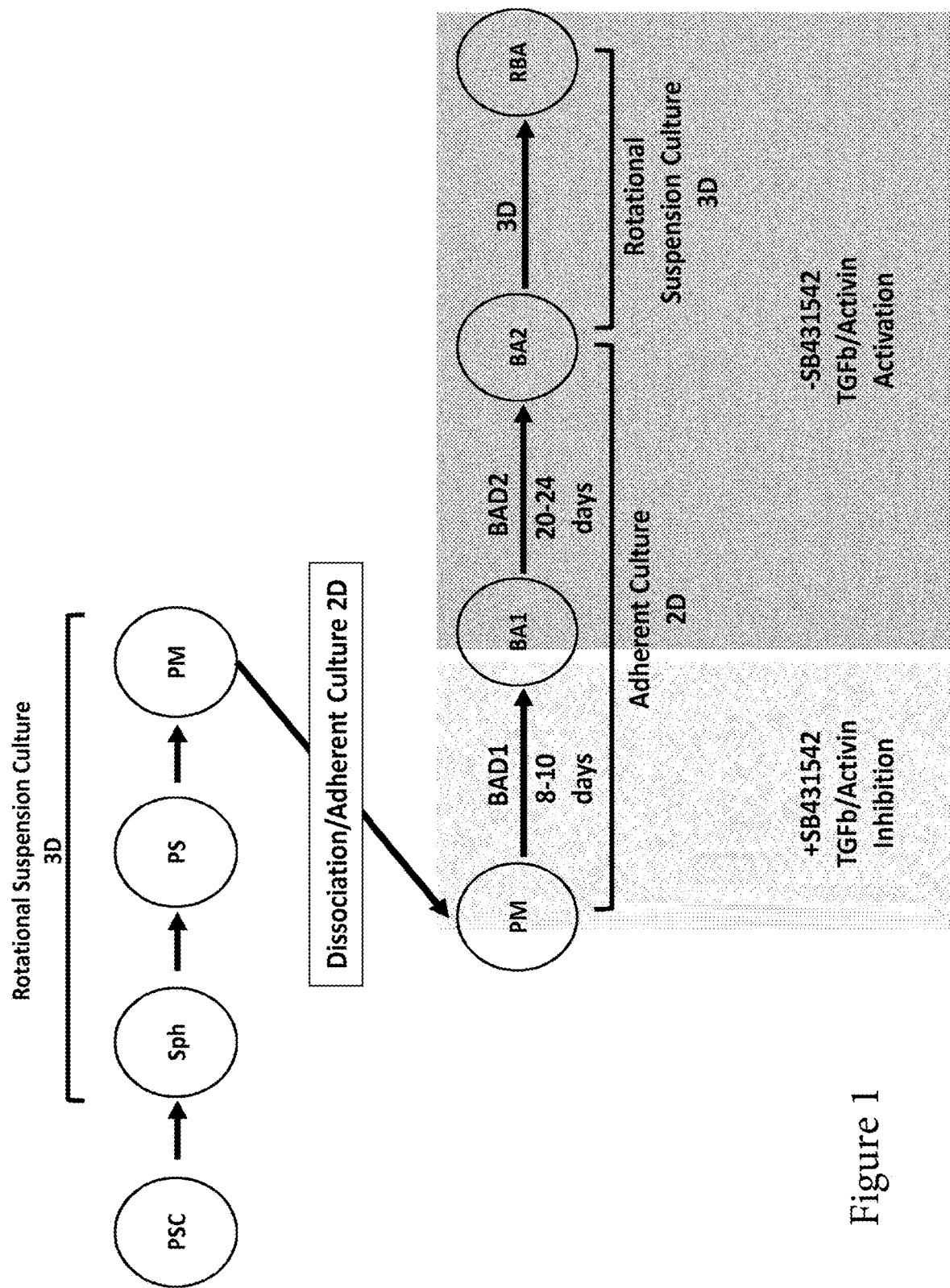
FIG. 1. Schematic Representation of the Method
Figure 2:
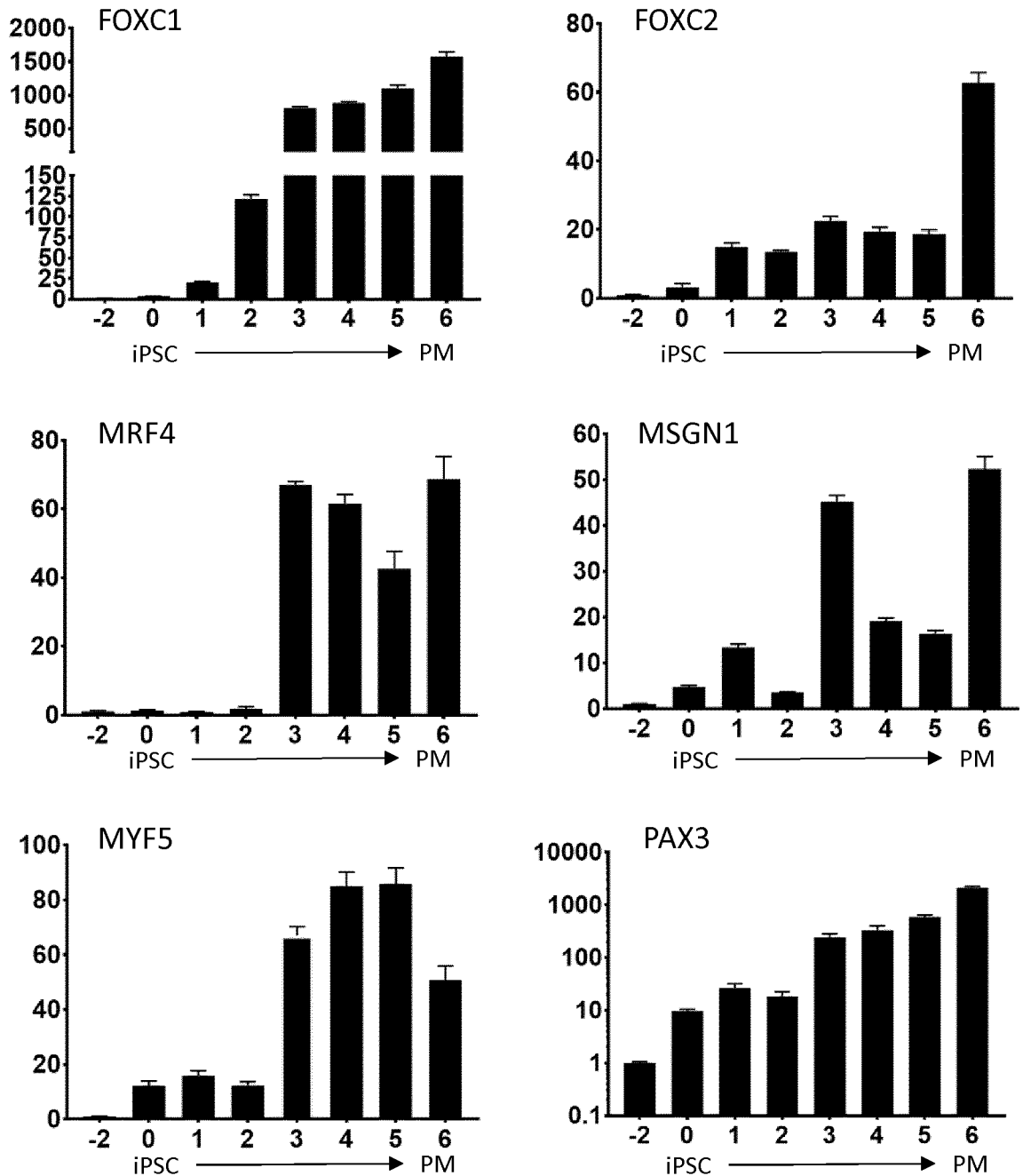
Figure 3:
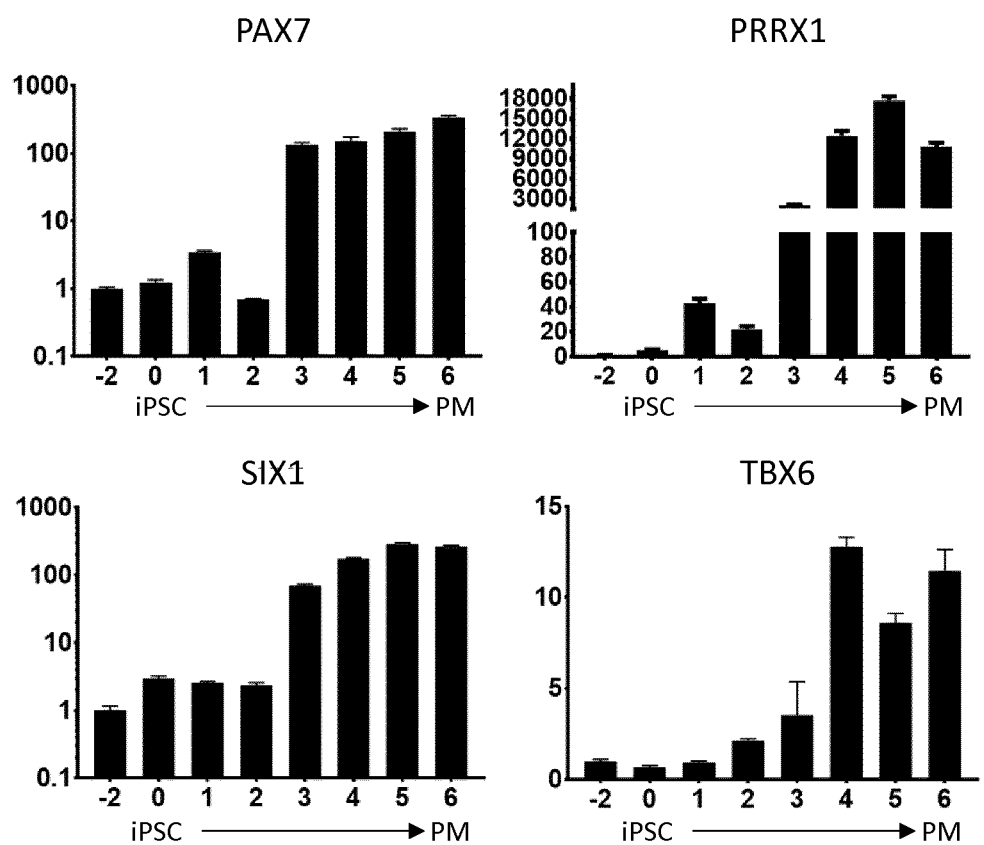

FIG. 2 and FIG. 3. Gene Expression Analysis from hiPSC to Paraxial Mesoderm (PM) Differentiated Cells qPCR time course of PM differentiation: day −2=iPSC medium+ROCK inhibitor, day 0=start of differentiation. X axis are the days with day 0 being the start of differentiation.

Figure 4:
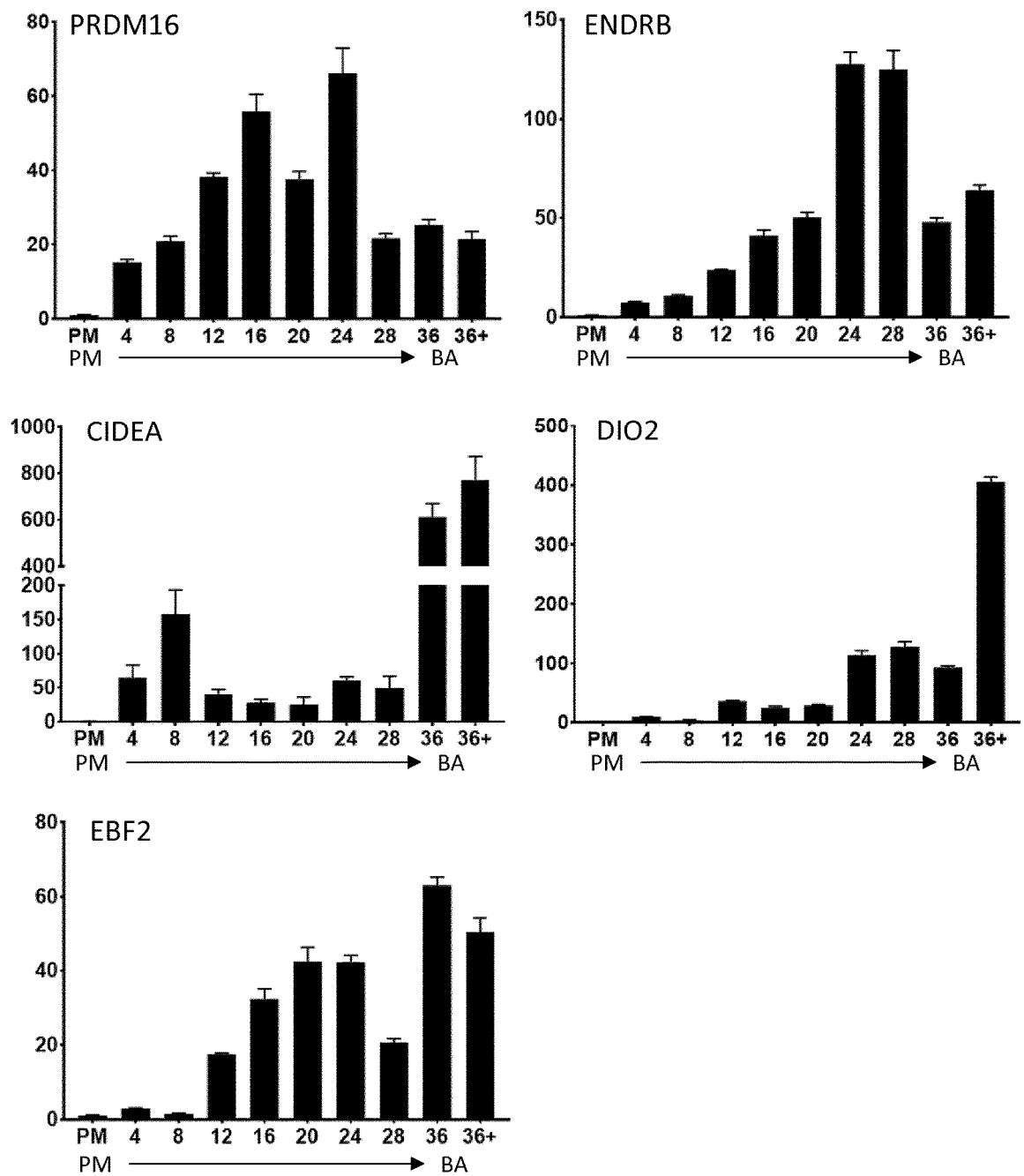
Figure 5:
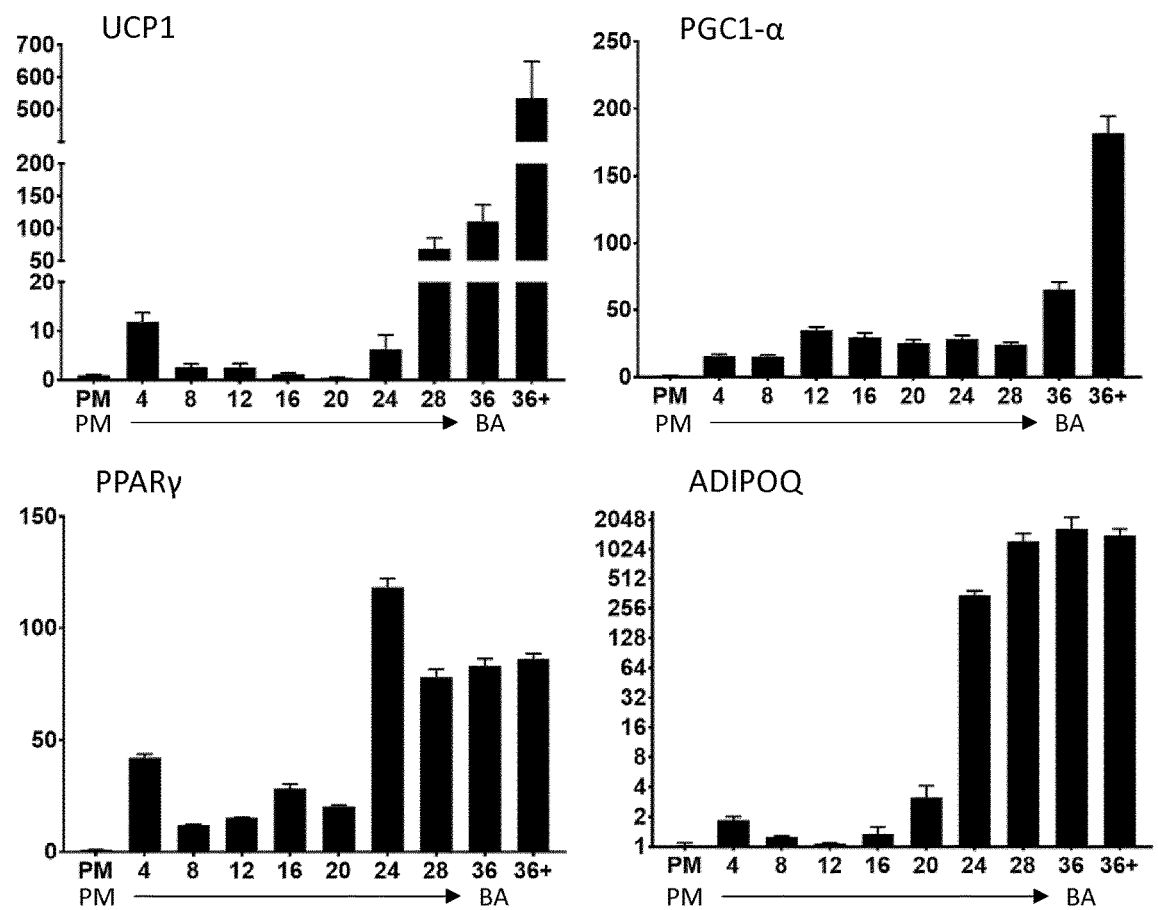

FIG. 4 and FIG. 5. Time Course Gene Expression Analysis for Selected Genes of Brown Adipocytes.

qPCR data for selected genes from paraxial mesoderm (PM) until day 36 of differentiation to brown adipocytes (BA). "+" indicates 4 hour exposure to 10 μM forskolin. All samples are relative to PM 18S rRNA expression.

Figure 6:
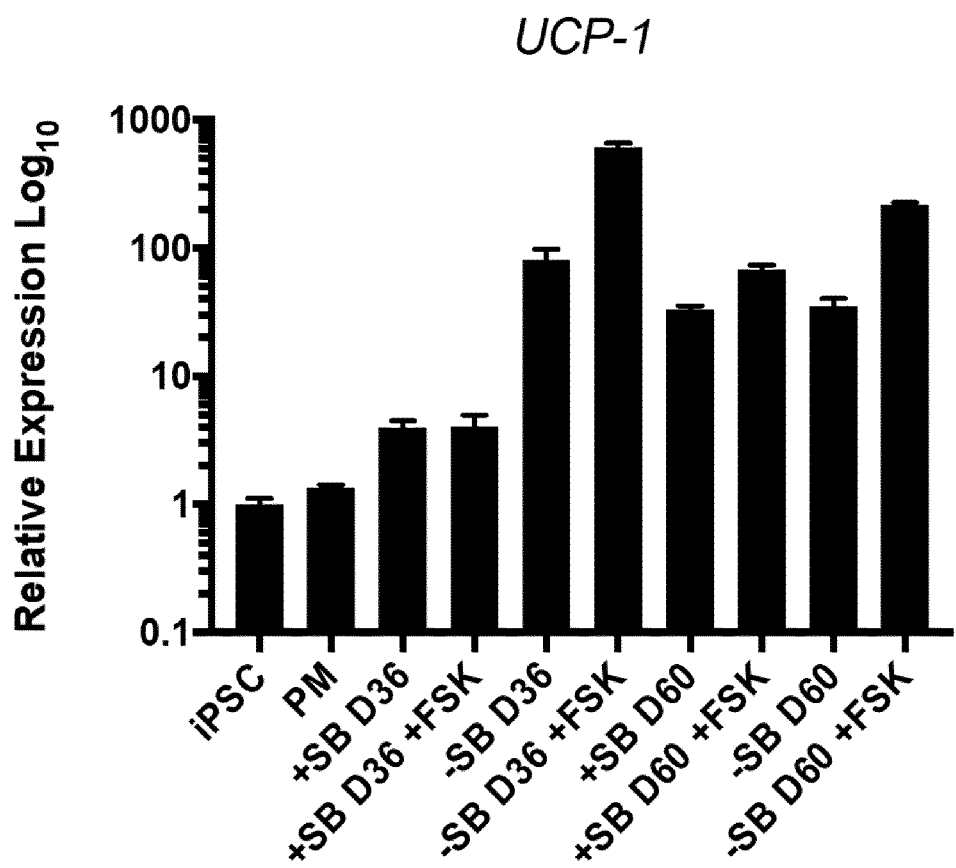

FIG. 6. Effect of TGF Beta Inhibition and Restitution of TGF Beta Signalling for BA Differentiation.

UCP1 expression analysis between long term (+SB) or short term (−SB) SB431542 exposure. Long term SB exposure includes SB431542 in the medium during the entire BA differentiation beginning immediately after plating dissociated paraxial mesoderm cells. Short term SB exposure includes SB431542 in the medium during only the first 8 days beginning immediately after plating dissociated paraxial mesoderm cells. Those samples marked "+FSK" received 10 μM Forskolin for 4 hours. Day numbers are the number of days after paraxial mesoderm differentiation. All samples are relative to iPSC using 18S rRNA as the endogenous control.

Figure 7:
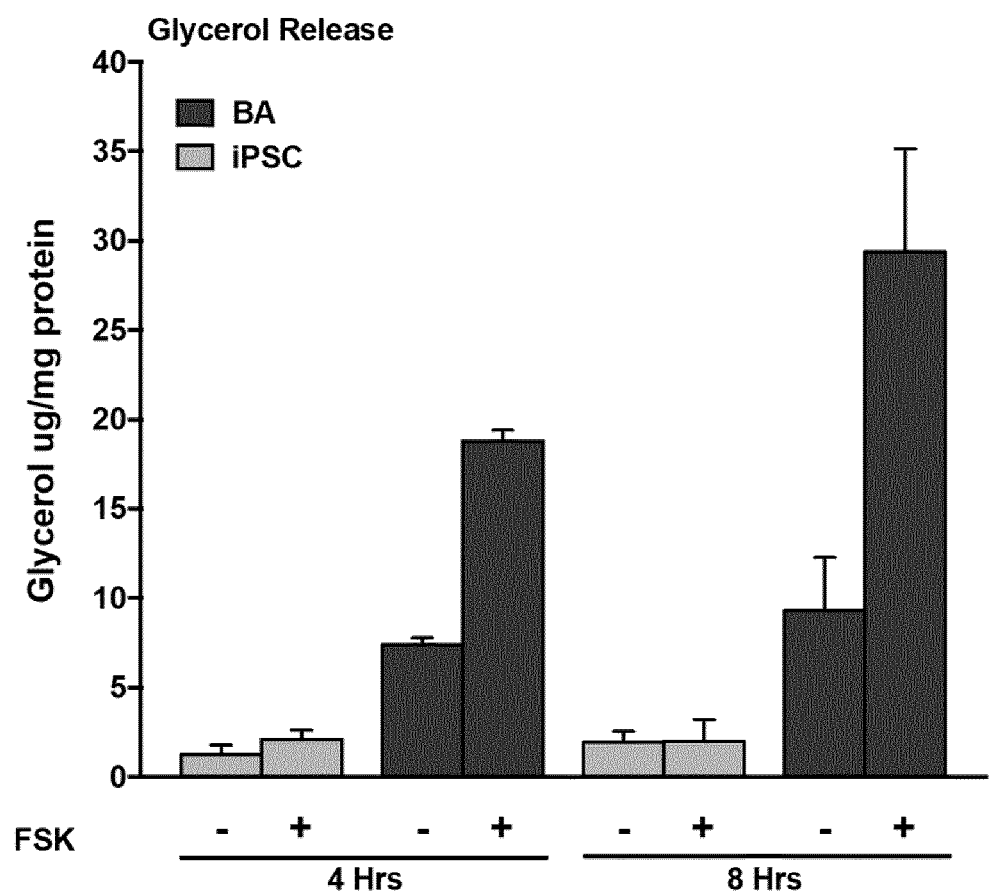

FIG. 7. Lipolytic Function.

This assay measure free glycerol released into the medium by cells through lipolysis. Cells that have activated lipolysis release greater amounts of free glycerol into the medium. The amount of this free glycerol is quantified by colorimetric comparison to a known standard (Abs @ 540 nm) Free Glycerol Reagent #F6428 (Sigma); Glycerol Standard #G7793 (Sigma).

Figure 8:
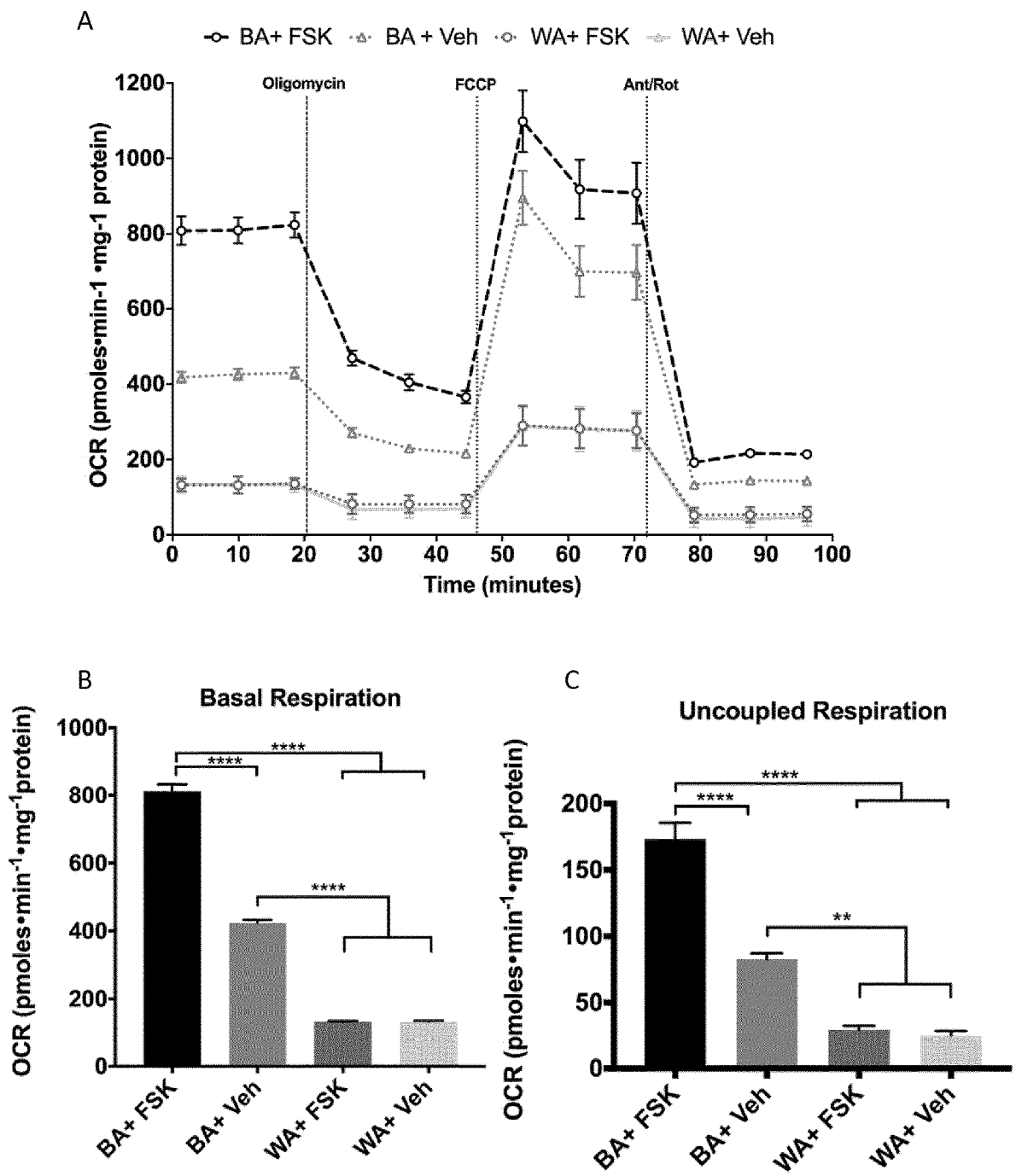

FIG. 8. Oxygen Consumption Profiles of Brown and White Adipocytes.

Differentiated brown and white adipocytes were grown to confluence in XF24 plates for 3 weeks and cultured in the presence (+) or absence (−) of overnight forskolin (FSK). FIG. 8(A) BA stimulated (black line-circle shape), BA unstimulated (black line-circle shape), WA stimulated (grey line-triangle shape), and WA unstimulated (grey line-square shape) profiles are shown. The histograms represent FIG. 8(B) mean basal respiration of each sample and FIG. 8(C) the uncoupling capacity of each sample.

Figure 9:
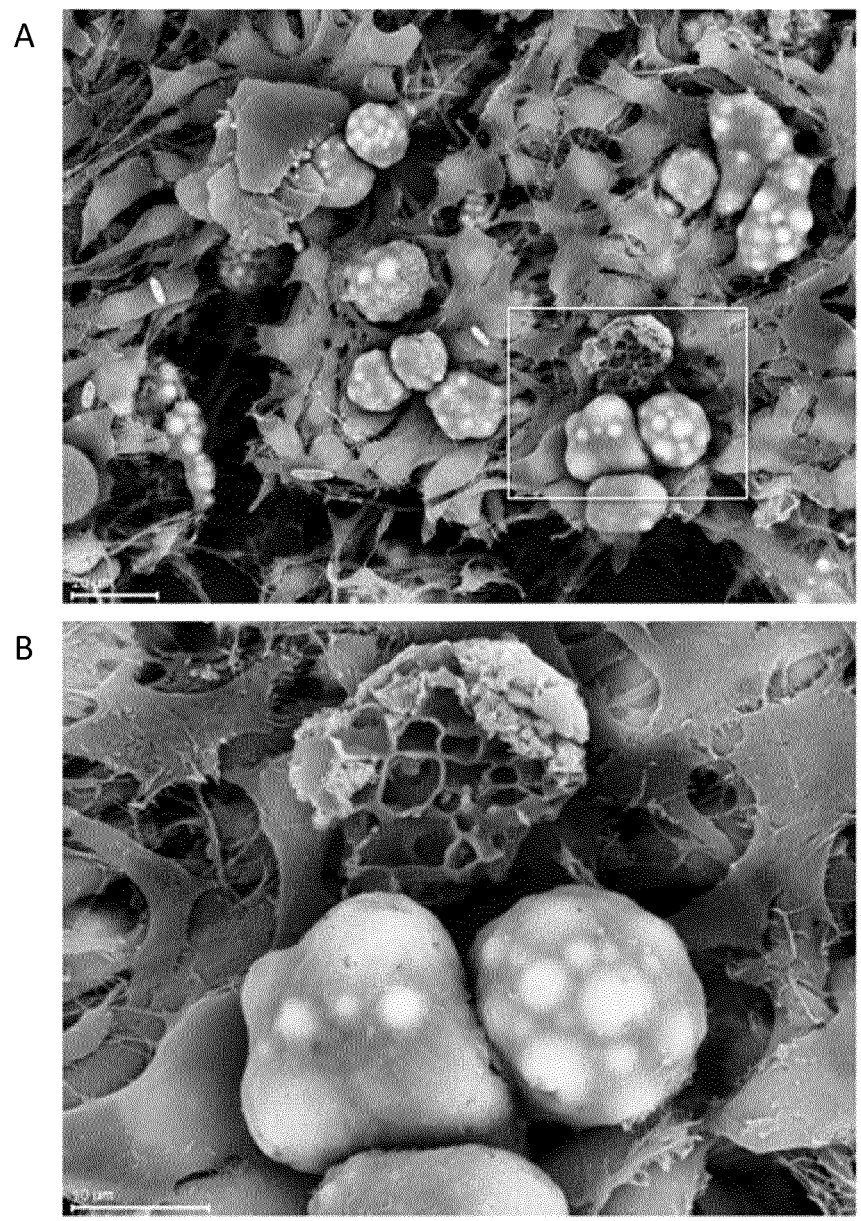

FIG. 9. Electronic Microscopy Imaging of BA Cells

Scanning electronic microscopy imaging of human iPSC derived BA cells at day 60 of differentiation representing multi-vesicular fat droplets packed in sacs. Imaging was performed on a Zeiss 1450EP SEM. (A) scale bar: 20 µm; (B) scale bar: 10 µm.

Figure 10:
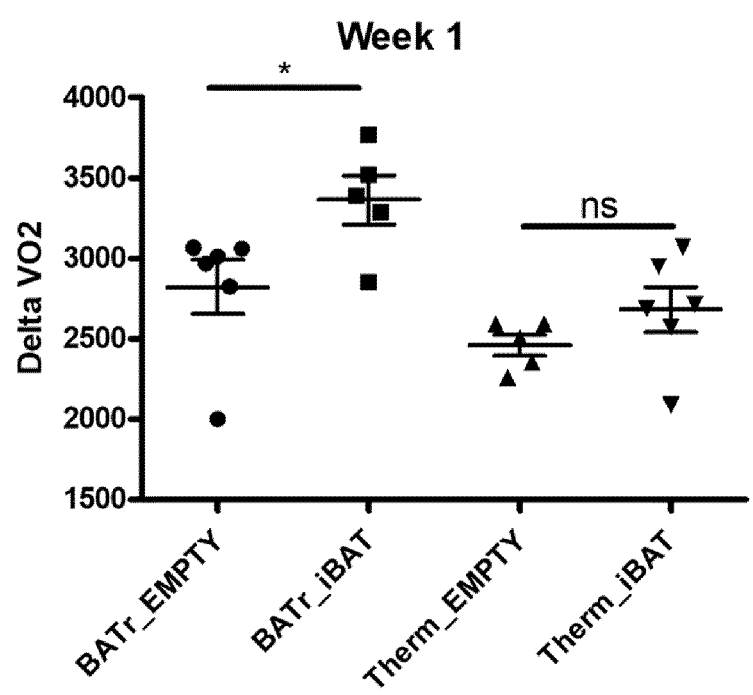

FIG. 10. In Vivo Calorimetric/Respiration Measurements after Human BA Cells Implantations Post NE Stimulation Measures of respiration quotient (DeltaVO2) of mice implanted with human BA cells (IBAT) or empty devices (EMPTY) treated with Norepinephrine (NE) for 1 hour. The mice are either surgically depleted for endogenous murine BA tissue (BATr) or treated at thermo-neutrality to inactivate the endogenous murine BA tissue (Therm).

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

A "production" of a population of brown adipocytes refers to production from a less mature precursor cell, for example a stem cell or a cell type on the differentiation pathway between a stem cell and a brown adipocyte (e.g. a mesoderm cell, preferably a paraxial mesoderm cell), by controlled differentiation of that precursor cell. The differentiation to provide the population of brown adipocytes of the invention may be carried out by culturing the population of precursor cells under suitable conditions which direct the differentiation of those cells in the desired manner, i.e. towards becoming brown adipocytes.

Brown Adipocytes

Brown adipose tissue (BAT), also known as brown fat, forms the adipose organ in combination with white adipose tissue (white fat). BAT is particularly prevalent in newborns and hibernating mammals. It is also present and metabolically active in adult humans, but its prevalence decreases as humans age.

The primary function of BAT is thermoregulation. In contrast to the heat produced by shivering muscle, BAT produces heat by non-shivering thermogenesis.

Brown adipocytes may be characterised by the expression of: UCP1, PGC1-α, PPARγ, ADIPOQ, PRDM16, ENDRB, CIDEA, D102 and/or EBF2.

In a preferred embodiment, the brown adipocytes express UCP1.

In another preferred embodiment, the brown adipocytes express UCP1, PGC1-α, PPARγ, ADIPOQ, PRDM16, ENDRB, CIDEA, D102 and/or EBF2 at least by day 36 of differentiation.

In another embodiment, the brown adipocytes exhibit greater uncoupled respiration and/or maximal respiration compared to white adipocytes and/or paraxial mesoderm cells.

In another embodiment, the brown adipocytes exhibit greater uncoupled respiration and/or maximal respiration when stimulated with FSK.

Brown adipocytes may also be characterised by the cells containing numerous (e.g. 2 or more) lipid droplets. This may distinguish brown adipocytes from white adipocytes, which contain a single lipid droplet.

Mitochondrial Uncoupling Protein (UCP1)

Mitochondrial uncoupling protein (UCP1), also known as thermogenin, is an uncoupling protein found in the mitochondria of BAT.

UCP1 functions to uncouple oxidative phosphorylation in brown adipocytes and enables generation of heat by non-shivering thermogenesis.

UCP1 is a marker for brown adipocytes.

An example amino acid sequence of human UCP1 is the sequence deposited under NCBI Accession No. NP 068605.1.

An example amino acid sequence of human UCP1 is:

```
                                          (SEQ ID NO: 1)
MGGLTASDVHPTLGVQLFSAGIAACLADVITFPLDTAKVRLQVQGECPTS

SVIRYKGVLGTITAVVKTEGRMKLYSGLPAGLQRQISSASLRIGLYDTVQ

EFLTAGKETAPSLGSKILAGLTTGGVAVFIGQPTEVVKVRLQAQSHLHGI

KPRYTGTYNAYRIIATTEGLTGLWKGTTPNLMRSVIINCTELVTYDLMKE

AFVKNNILADDVPCHLVSALIAGFCATAMSSPVDVVKTRFINSPPGQYKS

VPNCAMKVFTNEGPTAFFKGLVPSFLRLGSWNVIMFVCFEQLKRELSKSR

QTMDCAT
```

Mesoderm Cells

The mesoderm is one of the three primary germ layers (in addition to the ectoderm and endoderm) that is found in the early embryo in all bilaterian animals. The mesoderm is the middle layer formed between the ectoderm and endoderm.

The mesoderm forms mesenchyme, mesothelium, non-epithelial blood cells and coelomocytes. The mesoderm also forms the muscles and part of the gonads.

The paraxial mesoderm, also known as the presomitic or somitic mesoderm, is the part of the mesoderm in the neurulating embryo that forms at the same time as the neural tube. The cells of this region give rise to somites, which are areas of tissue found around both sides of the neural tube, and form muscle and the tissues of the back.

Paraxial mesoderm cells may be characterised by the expression of any one of: FOXC1, FOXC2, MRF4, MSGN1, MYF5, PAX3, PAX7, PRRX1, SIX1 and/or TBX6.

Transforming Growth Factor Beta (TGF-β)

Transforming growth factor beta 1 (TGF-β1) is a member of the transforming growth factor beta superfamily of cytokines and is a secreted protein that performs a number of functions, including in the control of cell growth, cell proliferation, cell differentiation and apoptosis.

In one embodiment, the TGF-β signalling inhibitor is a SMAD2 and SMAD3 inhibitor.

In one embodiment, the TGF-β signalling inhibitor is an activin A inhibitor.

In a preferred embodiment, the TGF-β signalling inhibitor is SB-431542.

In a preferred embodiment, the TGF-β signalling inhibitor is:

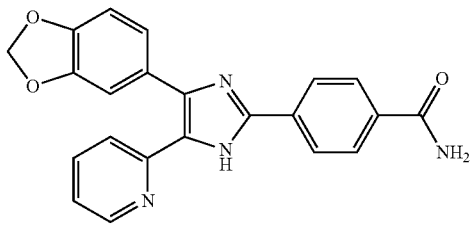

(I)

or a salt or derivative thereof.

The uses and methods of the invention may also use derivatives of compound (I) that provide a substantially equivalent function during the production of brown adipocytes from precursor cells.

The uses and methods of the invention may also use other TGF-β signalling inhibitors that provide a substantially equivalent function during the production of brown adipocytes from precursor cells. For example, other TGF-6 signalling inhibitors providing a substantially equivalent function include: SB525334, Galunisertib (LY2157299), GW788388, LY2109761, RepSox, LY364947, and SD208.

In one embodiment, the inhibitor is used in the invention at a concentration of about 1-50, 1-40, 1-30 or 1-20 µM. In another embodiment, the inhibitor is used in the invention at a concentration of about 1-20 µM.

In another embodiment, the inhibitor is used in the invention at a concentration of about 5-15, 6-14, 7-13, 8-12, 9-11 µM. In another embodiment, the inhibitor is used in the invention at a concentration of about 5-10 µM.

In another embodiment, the inhibitor is used in the invention at a concentration of about 1-5, 6-10, 11-15, 16-20, 21-25, 26-30, 31-35, 36-40, 41-45, or 46-50 µM. Preferably, the inhibitor is used in the invention at a concentration of about 1-50 µM, most preferable at about 10 µM.

UCP-1 Activator

A UCP-1 activator may be used to test the function of the brown adipocytes.

In one embodiment, a UCP-1 activator is added to increase expression of UCP-1, a marker of brown adipocytes.

In one embodiment, the UCP-1 activator is forskolin (FSK):

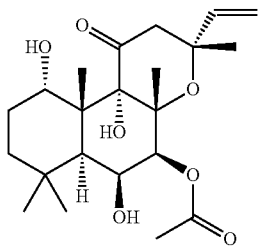

or a salt or derivative thereof.

In one embodiment forskolin (FSK) is added to stimulate the cells to increase UCP1 expression. In a preferred embodiment, 1-50 µM forskolin (FSK) is added for 6 to 24 hours.

Salts

The agents of the invention can be present as salts, in particular pharmaceutically-acceptable salts or esters.

Pharmaceutically-acceptable salts of the agents of the invention include suitable acid addition or base salts thereof. A review of suitable pharmaceutical salts may be found in Berge. et al. (1977) J. Pharm. Sci. 66: 1-19. Salts are formed, for example, with strong inorganic acids such as mineral acids, e.g. sulphuric acid, phosphoric acid or hydrohalic acids; with strong organic carboxylic acids, e.g. alkanecarboxylic acids of 1 to 4 carbon atoms which are unsubstituted or substituted (e.g. by halogen), such as acetic acid; with saturated or unsaturated dicarboxylic acids, e.g. oxalic, malonic, succinic, maleic, fumaric, phthalic or tetraphthalic acid; with hydroxycarboxylic acids, e.g. ascorbic, glycolic, lactic, malic, tartaric or citric acid; with amino acids, e.g. aspartic or glutamic acid; with benzoic acid; or with organic sulfonic acids, such as ($C_1$-$C_4$)-alkyl- or aryl-sulfonic acids, which are unsubstituted or substituted (e.g. by a halogen), such as methane- or p-toluene sulfonic acid.

Enantiomers/Tautomers

The invention also includes where appropriate all enantiomers and tautomers of the agent. The corresponding enantiomers and/or tautomers may be isolated/prepared by methods known in the art.

Stereo and Geometric Isomers

Some of the agents of the invention may exist as stereoisomers and/or geometric isomers. For example, they may possess one or more asymmetric and/or geometric centres and so may exist in two or more stereoisomeric and/or geometric forms. The invention contemplates the use of all the individual stereoisomers and geometric isomers of those agents, and mixtures thereof. The terms used in the claims encompass these forms, provided said forms retain the appropriate functional activity (though not necessarily to the same degree).

The invention also includes all suitable isotopic variations of the agent or pharmaceutically-acceptable salts thereof. An isotopic variation of an agent of the invention or a pharmaceutically-acceptable salt thereof is defined as one in which at least one atom is replaced by an atom having the same atomic number, but an atomic mass different from the atomic mass usually found in nature. Examples of isotopes that can be incorporated into the agent and pharmaceutically-acceptable salts thereof include isotopes of hydrogen, carbon, nitrogen, oxygen, phosphorus, sulphur, fluorine and chlorine, such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically-acceptable salts thereof, for example, those in which a radioactive isotope such as $^3H$ or $^{14}C$ is incorporated, are useful in drug and/or substrate tissue distribution studies. Tritiated, i.e. $^3H$, and carbon-14, i.e. $^{14}O$, isotopes are particularly preferred for their ease of preparation and detectability. Further, substitution with isotopes such as deuterium, i.e. $^2H$, may afford certain therapeutic advantages resulting from greater metabolic stability, for example, increased in vivo half-life or reduced dosage requirements and hence may be preferred in some circumstances. Isotopic variations of the agent of the invention and pharmaceutically-acceptable salts thereof of this invention can generally be prepared by conventional procedures using appropriate isotopic variations of suitable reagents.

Solvates

The invention also includes solvate forms of the agents of the invention. The terms used in the claims encompass these forms.

Polymorphs

The invention also relates to the agents of the invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Methods of Production

The brown adipocytes of the invention may be produced from a precursor cell, such as a stem cell and/or a mesoderm cell.

In one aspect the invention provides the use of a transforming growth factor beta (TGF-β) signalling inhibitor for producing a population of brown adipocytes in vitro.

In another aspect, the invention provides a method for producing a population of brown adipocytes comprising the step of contacting a population of cells with a transforming growth factor beta (TGF-β) signalling inhibitor.

The population of cells contacted with a transforming growth factor beta (TGF-β) signalling inhibitor is a population of precursor cells that has the capacity to differentiate into brown adipocytes when cultured under suitable conditions.

In one embodiment, the population of cells contacted with the TGF-β signalling inhibitor is produced, preferably in vitro, from a population of stem cells. In a preferred embodiment, the population of cells contacted with the TGF-β signalling inhibitor are produced using 3D cell culture. In a preferred embodiment, the stem cells are induced pluripotent stem cells.

3D cell culture is an artificially-created environment which enables cells to grow or interact with their surroundings in three dimensions. In such culture, cells typically form 3D colonies, which may be referred to as "spheroids". The 3D culture approach may more accurately model the cells' in vivo growth and behaviour.

The skilled person is readily able to carry out 3D cell culture, for example by taking advantage of any of a number of commercially-available culturing tools. For example, the 3D culture may be carried out using scaffold or scaffold-free techniques.

Scaffold-based techniques make use of supports such as solid scaffolds and hydrogels to enable the cells to form a 3D culture. Such scaffolds may aim to mimic the natural extracellular matrix (ECM), which is present in vivo.

Scaffold-free techniques dispense with the use of the scaffold on which to grow the cells. Instead, 3D spheroids may be established through the use of, for example, low-adhesion plates, hanging-drop plates, micro-patterned surfaces, rotating bioreactors, magnetic levitation and magnetic 3D bioprinting.

Establishment of a, for example, stem cell co-aggregate 3D spheroid may be achieved, for example, by culturing in ultra-low attachment plates and/or using a shaker platform at about 80-120 RPM or 90-110 RPM, preferably about 100 RPM. Establishment of the initial co-aggregate may be achieved following incubation, for example, for about 6-18 h or 9-15 h, preferably about 12 h.

In a preferred embodiment, the method comprises the steps:
 (a) culturing a population of cells, preferably a population of mesoderm cells, for a first period of time in the presence of the TGF-β signalling inhibitor; and
 (b) culturing the population of cells provided by step (a) for a second period of time in the absence of the TGF-β signalling inhibitor.

In one embodiment, the first period of time is about 1-15, 2-15, 3-15, 4-15, 5-15, 6-15, 7-15, 8-15, 1-14, 2-14, 3-14, 4-14, 5-14, 6-14, 7-14, 8-14, 1-13, 2-13, 3-13, 4-13, 5-13, 6-13, 7-13, 8-13, 1-12, 2-12, 3-12, 4-12, 5-12, 6-12, 7-12, 8-12, 1-11, 2-11, 3-11, 4-11, 5-11, 6-11, 7-11, 8-11, 1-10, 2-10, 3-10, 4-10, 5-10, 6-10, 7-10 or 8-10 days, preferably about 6-10 days.

In one embodiment, the second period of time is about 15-30, 16-30, 17-30, 18-30, 19-30, 20-30, 15-29, 16-29, 17-29, 18-29, 19-29, 20-29, 15-28, 16-28, 17-28, 18-28, 19-28, 20-28, 15-27, 16-27, 17-27, 18-27, 19-27, 20-27, 15-26, 16-26, 17-26, 18-26, 19-26, 20-26, 15-25, 16-25, 17-25, 18-25, 19-25, 20-25, 15-24, 16-24, 17-24, 18-24, 19-24 or 20-24 days, preferably about 15-30 days.

In a particularly preferred embodiment, the method comprises the steps:
 (a) culturing a population of cells, preferably a population of mesoderm cells, for about 1-15 days, preferably about 6-10 days, in the presence of the TGF-β signalling inhibitor; and
 (b) culturing the population of cells provided by step (a) for about 20-50 days, preferably about 15-30 days, in the absence of the TGF-β signalling inhibitor.

In one embodiment, the cultures of steps (a) and (b) are adherent cultures.

In one embodiment, the method comprises the further step of:
 (c) culturing the population of cells provided by step (b) under conditions suitable for the formation of aggregated brown adipocytes, preferably wherein the culture is a rotational suspension culture.

The cell cultures during the methods of the invention may be carried out using any suitable cell culture medium.

For example, culture may be carried out in a chemically-defined base medium (DBM) composed of DMEM/F-12 without glutamine, supplemented with 2% Probumin (e.g. from EMD Milipore, Billerica, MA), 1× Antibiotic-Antimyotic (e.g. from Corning, Corning, NY), 1× MEM non-essential amino acids (e.g. from Corning, Corning, NY), 1× Trace Elements A (e.g. from Corning, Corning, NY), 1× Trace Elements B (e.g. from Corning, Corning, NY), 1× Trace Elements C (e.g. from Corning, Corning, NY), 50 µg/mL Ascorbic Acid (e.g. from Sigma-Aldrich, St. Louis, MO), 10 µg/mL Transferrin (e.g. from Athens Research and Technology, Athens, GA), 0.1 mM 2-mercaptoethanol (e.g. from Thermo-Fisher, Waltham, MA) and 1× Glutagro (e.g. from Corning, Corning, NY). This medium may be further supplemented with the final concentrations of the following factors: 8 ng/mL bFGF (e.g. from R&D Systems, Minneapolis, MN), 100 ng/mL BMP7 (e.g. from R&D Systems, Minneapolis, MN), 200 ng/mL LONG® R3 IGF-I (e.g. from Sigma-Aldrich, St. Louis, MO), 10 µM Y-27632 dihydrochloride (e.g. from Tocris, Minneapolis, MN), 2 µM Rosiglitazone (e.g. from Tocris, Minneapolis, MN), 1 µM Dexamethasone (e.g. from Tocris, Minneapolis, MN), 1 nM LT-3 (3,3',5-Triiodo-L-thyronine sodium salt) (e.g. from Sigma-Aldrich, St. Louis, MO) and 500 µM IBMX (3-Isobutyl-1-methylxanthine) (e.g. from Sigma-Aldrich, St. Louis, MO).

The culture medium may be supplemented with a suitable concentration of the TGF-β signalling inhibitor. For culturing in the absence of the TGF-β signalling inhibitor, the medium may be supplemented with, for example, 1:500 Chemically Defined Lipid Concentrate (e.g. from ThermoFisher, Waltham, MA).

Suitable culture conditions for use in the methods of the invention include, for example:

(a) culturing at about 36-38° C. or 36.5-37.5° C., preferably about 37° C.;
(b) culturing at about 4-6% or 4.5-5.5% $CO_2$, preferably about 5% $CO_2$; and/or
(c) culturing at at least about 95%, 96%, 97%, 98% or 99% humidity, preferably about 100% humidity.

Stem Cells

The brown adipocytes of the invention may be produced (e.g. in vitro) from stem cells.

Stem cells are cells that have the capacity to differentiate into more specialised cells and can also divide to produce more stem cells.

The methods of the invention may comprise contacting a population of precursor cells (e.g. a population of mesoderm cells, preferably a population of paraxial mesoderm cells) with a transforming growth factor beta (TGF-β) signalling inhibitor, wherein the population of precursor cells has itself been produced (e.g. in vitro) by the differentiation of a population of stem cells.

Thus, the methods of the invention may comprise the step of producing a population of cells (e.g. in vitro) from a population of stem cells.

Preferably, the stem cells of the invention are pluripotent stem cells.

Pluripotent stem cells are stem cells that may propagate indefinitely and differentiate into all cell types of the human body. These stem cells hold promise in providing a single source of cells that may replace cells affected by damage or disease.

Pluripotent stem cells may be created through a number of techniques. Preferably, the stem cells of the invention are induced pluripotent stem cells (iPSCs).

iPSCs are a type of pluripotent stem cell that may be created directly from adult cells. The skilled person is readily able to prepare iPSCs, for example by introducing specific transcription factors into adult cells or contacting adult cells with specific protein combinations.

iPSCs are advantageous over embryonic stem cells in that they overcome the need for using embryonic material and can be prepared from a subject to which they (or cells produced from them) are later re-introduced. Such autologous cell transplantation may overcome the risk of immune rejection of transplanted material.

The stem cells of the invention may, in particular, be those produced without destruction of an embryo.

Methods are known in the art for producing pluripotent stem cells, without the destruction of an embryo. In particular, it has been shown that mouse and human embryonic stem cells may be produced from single blastomeres while leaving the embryo intact. For example Chung, Y. et al. (2006) Nature 439: 216-219 describes methods for making mouse embryonic stem cells from a single blastomere. Later advances on this procedure provided methods where co-culturing the blastomere cell lines with other ESCs is not required (Chung, Y. et al. (2008) Cell Stem Cell 2: 113-117).

Preferably the stem cells of the invention are mammalian stem cells, preferably human stem cells.

Diseases

The brown adipocytes of the invention may be used in the treatment or prevention of diseases characterised by high blood sugar levels over a prolonged period. Such conditions include insulin resistance; prediabetes; type 1 or 2 diabetes; metabolic syndrome and obesity associated conditions.

Insulin resistance is a condition in which the body produces insulin but does not use it effectively. When subjects have insulin resistance, glucose builds up in the blood instead of being absorbed by the cells, leading to type 2 diabetes or prediabetes. Insulin resistance may be defined as a reduced responsiveness of a target cell or a whole organism to the insulin concentration to which it is exposed. This definition is generally used to refer to impaired sensitivity to insulin-mediated glucose disposal.

Prediabetes is the medical stage in which not all of the symptoms required to diagnose a person as diabetic are present, but blood sugar is abnormally high. Prediabetes usually occurs in subjects who already have insulin resistance. Although insulin resistance alone does not cause type 2 diabetes, it often sets the stage for the disease by placing a high demand on the insulin-producing beta cells. In prediabetes, the beta cells can no longer produce enough insulin to overcome insulin resistance, causing blood glucose levels to rise above the normal range.

Diabetes mellitus (commonly referred to as diabetes) is a group of metabolic diseases that are characterised by high patient blood sugar levels over a prolonged period. The two main types of diabetes (type 1 and type 2) have different causes and methods of treatment.

Type 1 diabetes results from the destruction of the insulin-producing beta cells in the pancreas, commonly through autoimmune mechanisms.

Type 2 diabetes results from insulin resistance in peripheral tissues, which may be combined with pancreatic beta cell dysfunction.

Type 2 diabetes is a chronic metabolic disorder which is increasing in prevalence globally. In some countries of the world the number of subjects affected is expected to double in the next decade due to an increase in the ageing population.

Type 2 diabetes is characterised by insulin insensitivity as a result of insulin resistance, declining insulin production and eventual pancreatic beta-cell failure. This leads to a decrease in glucose transport to the liver, muscle cells and fat cells. There is an increase in the breakdown of fat associated with hyperglycaemia.

As a result of this dysfunction, glucagon and hepatic glucose levels that rise during fasting are not suppressed with a meal. Given inadequate levels of insulin and increased insulin resistance, hyperglycaemia results.

Subjects with type 2 diabetes are more vulnerable to various short- and long-term complications, including diabetic ketoacidosis (DKA), hyperosmolar hyperglycaemic state (HHS), retinopathy, cardiopathy, nephropathy and neuropathy. These complications may lead to premature death.

Metabolic syndrome is a clustering of at least three of five of the following medical conditions: abdominal (central) obesity, elevated blood pressure, elevated fasting plasma glucose, high serum triglycerides and low high-density lipoprotein (HDL) levels. Metabolic syndrome is associated with the risk of developing cardiovascular disease and diabetes.

Obesity is a medical condition which is generally measured by BMI over 30 kg/m2 which is calculated by dividing a person's weight by the square of the person's height. Obesity increases the likelihood of various diseases or conditions particularly cardiovascular disease, type 2 diabetes, certain types of cancer, osteoarthritis and depression.

Method of Analysis

In one aspect, the invention provides a method of analysing brown adipocytes.

The invention provides access to populations of brown adipocytes that was not previously possible, thus enabling studies to be carried out on these populations to further characterise the function and behaviour of these cells.

Preferably the methods of analysis are carried out in vitro. However, the brown adipocytes of the invention may also be analysed by implanting the population of brown adipocytes into an animal model, for example a mouse model.

Suitable methods of analysis include, but are not limited to, flow cytometry, immunoassays and cell imaging-based studies (e.g. fluorescence microscopy), which are well known techniques in the art.

Method of Treatment

In one aspect, the invention provides the population of brown adipocytes of the invention for use in surgery and/or therapy, for example in treating or preventing diabetes.

The treatment or prevention may comprise transplantation of the population of brown adipocytes of the invention to a subject in need thereof. Thus, the invention provides a method of treating or preventing diabetes comprising the step of transplanting the population of brown adipocytes of the invention to a subject in need thereof.

The diabetes to be treated or prevented may, for example, be type 1 or type 2 diabetes.

It is to be appreciated that all references herein to treatment include curative, palliative and prophylactic treatment; although in the context of the present invention references to preventing are more commonly associated with prophylactic treatment. The treatment of mammals, particularly humans, is preferred. Both human and veterinary treatments are within the scope of the present invention.

Transplantation

The terms "transplant" and "implant" are used interchangeably herein.

The population of brown adipocytes of the invention may, for example, be administered to a subject as part of an autologous cell transplant procedure or as part of an allogeneic cell transplant procedure.

The term "autologous cell transplant procedure" refers to a procedure in which the precursor cells (from which the population of brown adipocytes of the invention are produced) are obtained from the same subject as that to which the population of brown adipocytes of the invention are administered.

Autologous transplant procedures are advantageous as they avoid problems associated with immunological incompatibility and are accessible to subjects irrespective of the availability of a genetically matched donor.

The term "allogeneic cell transplant procedure" refers to a procedure in which the precursor cells (from which the population of brown adipocytes of the invention are produced) are obtained from a different subject as that to which the population of brown adipocytes of the invention are administered. Preferably, the donor will be genetically matched to the subject to which the population of brown adipocytes are administered to minimise the risk of immunological incompatibility.

Suitable doses of the population of brown adipocytes of the invention are such as to be therapeutically and/or prophylactically effective. The dose to be administered may depend on the subject and condition to be treated, and may be readily determined by a skilled person.

The population of brown adipocytes may be implanted into a subject as part of a cosmetic surgery procedure.

The population of brown adipocytes may be implanted into a subject as part of a plastic surgery procedure, for example reconstructive plastic surgery, such as that which may be carried out after an accident or burn injury.

Pharmaceutical Composition

The cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Materials and Methods

Cell Culture and Differentiation

The human pluripotent stem cells (PSC) were seeded at 50,000 cells/cm$^2$ on polystyrene culture plates (Thermo-Fisher, Waltham, MA) coated with Geltrex LDEV-Free hESC qualified reduced growth factor basement membrane matrix (Thermo-Fisher, Waltham, MA) at a 1:200 dilution in DMEM/F-12 without glutamine (Corning, Corning, NY). Media for PSC maintenance, sphere formation, paraxial mesoderm and brown adipocyte differentiations were accomplished using a chemically defined base medium (DBM) supplemented with specific factors. DBM was composed of DMEM/F-12 without glutamine supplemented with 2% Probumin (EMD Milipore, Billerica, MA), 1× Antibiotic-Antimyotic (Corning, Corning, NY), 1× MEM non-essential amino acids (Corning, Corning, NY), 1× Trace Elements A (Corning, Corning, NY), 1× Trace Elements B (Corning, Corning, NY), 1× Trace Elements C (Corning, Corning, NY) 50 μg/mL Ascorbic Acid (Sigma-Aldrich, St. Louis, MO), 10 μg/mL Transferrin (Athens Research and Technology, Athens, GA), 0.1 mM 2-mercaptoethanol (Thermo-Fisher, Waltham, MA) and 1× Glutagro (Corning, Corning, NY). The PSC maintenance medium (MM) was composed of DBM supplemented with 8 ng/mL human basic-FGF (R&D Systems, Minneapolis, MN), 200 ng/mL LONG® R3 human IGF-I (Sigma-Aldrich, St. Louis, MO), 10 ng/mL Activin A (R&D Systems, Minneapolis, MN) and 10 ng/mL human Heregulin β-1 (Peprotech, Rocky Hill, NJ) to comprise a complete defied media (CDM). Human PSCs were cultured in CDM with media changes every 24 h up to 90% confluency, or 4 days, with 5% $CO_2$ in a 37° C. incubator. Human PSCs were removed from culture plates for passaging using Accutase® (Innovative Cell Technologies, San Diego, CA) at room temperature (RT) for 5-10 minutes. Following centrifugation at 1000 rpm for 4 minutes at RT, Accutase was aspirated off and the cell pellet was resuspended in CDM, cell number was then quantified using a haemocytometer. Cells were reseeded onto geltrex-coated plates as described above. Positive expression of OCT3/4, SOX2 and NANOG via quantitative polymerase chain reaction (qPCR), and immunofluorescence confirmed cell identity.

Paraxial Mesoderm (PM) Differentiation

Paraxial Mesoderm (PM) cells were generated in a three-step process using rotational suspension culture. First a single-cell suspension of hPSCs containing $1\times10^6$ cells/mL was seeded in 6-well suspension plates (Greiner Bio-One, Monroe, NC) at a volume of 5.5 mL in sphere formation medium (SFM). The plate was then placed on an Innova 2000 platform shaker (New Brunswick Scientific, Edison, NJ) at 97 RPM in a 5% $CO_2$, 37° C. incubator. Sphere formation medium was composed of hPSC MM supplemented with 10 µM Y-27632 dihydrochloride (Tocris, Minneapolis, MN) for 24 hours. Spent medium was changed by transferal of spheres and medium via pipette to a conical tube and spheres allowed to gravity sediment up to 10 minutes. Carefully, the spent medium was aspirated without disturbing the sedimented spheres. After 24 hours in SFM, the medium was replaced with only hPSC MM for an additional 24 hours and the spheres returned to the suspension plate and returned to the orbital shaker. After 24 hours in MM, the medium was exchanged for paraxial mesoderm medium 1 (PMM1) via the medium exchange method above. PMM1 was composed of DBM supplemented with the final concentrations of the following factors: 10 ng/mL BMP4 (R&D Systems, Minneapolis, MN), 20 ng/mL bFGF (R&D Systems, Minneapolis, MN), 200 ng/mL LONG® R3 IGF-I (Sigma-Aldrich, St. Louis MO), and 250 nM Rapamycin (Tocris, Minneapolis, MN). After 24 hours, fresh PMM1 was exchanged for spent PMM1 for another 24 hours. After a total of 48 hours in PMM1, the medium was exchanged with DBM to wash the cells. The cells were allowed to resediment, the DBM aspirated off and the spheres resuspended in PMM2 for an additional 96 hours with medium exchanges every 24 hours as above. As before the spheres were kept in suspension plates on the platform shaker. PMM2 was composed of DBM supplemented with the final concentrations of the following factors: 20 ng/mL bFGF (R&D Systems, Minneapolis, MN), 200 ng/mL LONG® R3 IGF-I (Sigma, Sigma-Aldrich, St. Louis MO), 250 nM Rapamycin (Tocris, Minneapolis, MN), 25 ng/mL Wnt3a, 50 ng/mL Noggin (R&D Systems, Minneapolis, MN), (R&D Systems, Minneapolis, MN), 2 µM Bio (Tocris, Minneapolis, MN), and 5 µM Forskolin (Tocris, Minneapolis, MN).

Brown Adipocyte (BA) Differentiation

Brown adipocyte (BA) differentiation was accomplished using two sequential media formulations designated BAD1 and BAD2. BAs were derived by first dissociating the PM spheres into single-cell suspension. Briefly, PM spheres were removed from the suspension plates and allowed to gravity sediment in a conical tube. The medium was aspirated carefully and the spheres gently washed once with excess DPBS without calcium or magnesium. The spheres were allowed to settle and the DPBS aspirated. The spheres were resuspended in 5 mL of RT Accumax® (Innovative Cell Technologies, San Diego, CA) and placed on a single speed rotating mixer for 20-30 minutes until a single-cell suspension was achieved. The cells were subsequently filtered through a 100 µm filter (ThermoFisher, Waltham, MA) into a 50 mL conical tube, washed with DPBS and centrifuged at 200 g for 4 minutes at RT; the resulting supernatant was aspirated and the cells resuspended in BAD1 medium for counting using a haemocytometer. BAD1 was composed of DBM supplemented with the final concentrations of the following factors: 8 ng/mL bFGF (R&D Systems, Minneapolis, MN), 100 ng/mL BMP7 (R&D Systems, Minneapolis, MN), 200 ng/mL LONG® R3 IGF-I (Sigma-Aldrich, St. Louis, MO), 10 µM Y-27632 dihydrochloride (Tocris, Minneapolis, MN), 2 µM Rosiglitazone (Tocris, Minneapolis, MN), 1 µM Dexamethasone (Tocris, Minneapolis, MN), 1 nM LT-3 (3,3',5-Triiodo-L-thyronine sodium salt) (Sigma-Aldrich, St. Louis, MO), 500 µM IBMX (3-lsobutyl-1-methylxanthine) (Sigma-Aldrich, St. Louis, MO), and 10 µM SB 431542 (Tocris, Minneapolis, MN). Cells were then seeded at a density of 90,000 cells/cm² on polystyrene culture plates (Thermo-Fisher, Waltham, MA) coated with Geltrex LDEV-Free hESC qualified reduced growth factor basement membrane matrix (Thermo-Fisher, Waltham, MA) at a 1:200 dilution in DMEM/F-12 without glutamine (Corning, Corning, NY). Cells were cultured in BAD1 until 100% confluence (8-10 days), with media changes every 24 hours. After 8-10 days, BAD1 was switched to BAD2. BAD2 is formulated the same as BAD1 excluding SB 431542 and supplemented with 1:500 Chemically Defined Lipid Concentrate (ThermoFisher, Waltham, MA). The cells were to remain in BAD2 until they are assayed or reaggregated for further use (e.g. transplantation or further in vitro analysis). BAD2 medium was changed daily. Reaggregation was achieved by first aspirating spent BAD2 medium and washing BA plates with DBPS; the cells are dissociated using a collagenase admixture containing 400 units each of collagenase I, II, and IV (ThermoFisher, Waltham, MA) diluted in HBSS without calcium and magnesium (Corning, Corning NY). The collagenase admixture was supplemented with 0.5 mM $CaCl_2^+$ (Sigma-Aldrich, St. Louis, MO) to increase enzymatic activity. BA cells are incubated in the collagenase admixture at 37° C. until the cells loosen from the plate (~20-30 mins) at which point they were mainly in a sheet. The plates containing the cells and collagenase were rinsed with an equal volume of EDTA dissociation solution (Beers et al., 2012), transferred to a conical tube and centrifuged at 200 g×4 minutes at RT. The supernatant is removed and the cells are then resuspended in 5 mL of Accumax® (Innovative Cell Technologies, San Diego, CA) and placed on a single speed nutating mixer for 20-30 minutes until a single-cell suspension was achieved. The cells are subsequently filtered through a 100 µm filter (ThermoFisher, Waltham, MA) into a 50 mL conical tube, washed with DPBS and centrifuged at 200 g for 4 minutes at room temperature; the resulting supernatant was aspirated and the cells resuspended in BAD2 medium and placed in 6-well suspension plates (Greiner Bio-One, Monroe, NC) at a volume of 5.5 mL/well. In general, one 10 cm plate of BA will yield enough cells for two wells of a 6-well plate for reaggregation, as there is loss between dissociation, filtration, wash and cell death. The suspension plates were placed on an Innova 2000 platform shaker (New Brunswick Scientific, Edison, NJ) at 97 RPM in a 5% $CO_2$, 37° C. incubator, and BAD2 replaced every other day by the gravity sedimentation medium exchange method above.

Adipocyte derived stem cells (ADSCs) were purchased from Thermofisher and cultured in MesenPRO™ RS medium (ThermoFisher, Waltham, MA) at a density of 5,000 cells/cm² until reaching 70% confluence. The cells were dissociated with 1× TrypLe (ThermoFisher, Waltham, MA) and seeded at a density of 10,000 cells/cm² for four days in MesenPRO™ RS medium. After four days the cells were at confluence and the medium was switched to StemPRO® Adipogenesis Differentiation Medium (ThermoFisher, Waltham, MA) to drive the cells toward a white adipocyte fate. The cells were culture for 21 days before being assayed.

qRT-PCR

Cells were lysed directly in the dish using TRK Lysis Buffer (Omega Bio-Tek, Norcross, GA) supplemented with 2-mercaptoethanol after DBPS wash and harvested on ice. E.Z.N.A RNA isolation kit (Omega Bio-Tek, Norcross, GA) was used to isolate RNA following the manufacturer's protocols and the RNA quantitated with a Biotek Synergy 2 plate reader. cDNA was synthesised using 1 µg of RNA via the Iscript cDNA synthesis kit (Bio-Rad, Hercules, CA) following the manufacturer's protocols. The cDNA was then diluted to a final volume of 500 µL with molecular grade water. ΔΔCt qRT-PCR analysis was performed using a ViiA7 Real-Time PCR System (Life Technologies, Carlsbad, CA) in a 384 well plate with a reaction of 5 µL TaqMan Universal PCR Master Mix No AmpErase UNG (appliedbiosystems), 0.5 µL TaqMan primer (Life Technologies), 0.5 µL molecular grade water and 4 µL cDNA for Tagman® probes used. Expression of each transcript was normalised to 18S ribosome, performed in triplicate and plotted as the mean±standard error.

Immunofluorescent Microscopy

Human pluripotent stem cells were cultured in Labtek 4-well chamber slides (ThermoFisher, Waltham, MA) at a density of 50,000/cm$^2$. Adipocyte derived stem cells were seeded at 10,000 cells/cm$^2$. Brown adipocytes were seeded as reaggregates at 15 reaggregates/cm$^2$, or roughly one well of a 6-well suspension plate to eight Labtek slides. Paraxial mesoderm spheres were collected in 15 mL falcon tubes using gravity sedimentation (10 mins), spent medium aspirated, spheres washed once with excess 1× DPBS without $Ca^{2+}$ or $Mg^{2+}$ and allowed to sediment again, supernatant aspirated and then fixed. The inclusion of MitoTracker® dye requires live cells with proper mitochondrial membrane potential. Therefore, if included, MitoTracker Deep Red dye was added to growth media at 200 nM for 30-45 minutes prior to fixation. All cells were fixed with 4% paraformaldehyde (Electron Microscopy Sciences, Hatfield, PA) for 30 minutes at room temperature. Fixed spheres were washed once with excess 1× DPBS without Ca' or $Mg^{2+}$ and allowed to sediment. The wash was removed and a solution of 15% sucrose was added to a volume sufficient to cover the spheres. This entire volume of sucrose and spheres was then overlaid to the surface of a 2 mL volume of 30% sucrose solution overnight at 4° C. as a cryoprotectant. After overnight dehydration in sucrose, the spheres were removed via wide bore 200 µL pipette tip and transferred into cryomolds filled with Tissue-Tek® O.C.T. Compound (Sakura Finetek, USA). The cryomolds were then transferred to liquid nitrogen gas phase for flash freezing for 5 minutes. Frozen cryomolds were stored at −80° C. and were subsequently sectioned using a Leica CM 3050 S cryostat (Leica Biosystems, Buffalo Grove, IL) at a thickness of 7 µm onto microscope slides and stored at −80° C.

Human PSCs were cultured to 80% confluence before fixation. Human ADSCs were cultured in StemPRO® Adipogenesis Differentiation Medium for 21 days. Brown adipocytes were cultured 14 to 30 days after seeding reaggregates. All samples, fixed cells and sections, were washed with 1× DPBS without Ca' or Mg' for 5 minutes. For hPSCs and PM the wash was removed and replaced with permeabilisation and blocking buffer containing PBST (1× PBS and 0.2% Triton X-100) (ThermoFisher, Waltham, MA), 10% donkey serum (Equitech-Bio), 0.3 M glycine (Sigma-Aldrich, St. Louis, MO) for 1 hour at room temperature. For BA cells, the wash was removed and replaced with permeabilisation and blocking buffer containing PBSS (1× PBS and 0.1% Saponin) (Millipore, Billerica, MA), 10% donkey serum, 0.3 M glycine for 1 hour at room temperature. For all, permeabilisation and blocking buffer was removed and the slides rinsed once with primary antibody incubation buffer containing PBST or PBSS and 10% donkey serum. Subsequent to removing the was the wash, primary antibodies (see Table 1) were prepared in primary antibody incubation buffer, added to samples and incubated overnight at 4° C. After overnight incubation with primary antibody, the samples were washed 3× with incubation buffer alone. Secondary antibodies were diluted in a 2.5% donkey serum, 0.2 M PBST/S solution and incubated for 1 hour at room temperature in the dark. Following removal of secondary antibodies, cells were washed twice with DPBS for 5 minutes each. If included, LipidTox Green/Red Dyes were added at 1:200 dilution in DPBS for 30 minutes. Subsequent to LipidTox dyes, 1 µg/mL 4',6-Diamidino-2-phenylindole dihydrochloride (Sigma-Aldrich, St. Louis, MO) in DPBS was added to cells for 5 minutes. After 3 washes in DPBS, coverslips were mounted to slides with ProLong Gold Antifade (ThermoFisher, Waltham, MA). A Leica DM6000B microscope and Zeiss LSM 710 confocal microscope were used to obtain images. Images were processed with Slidebook 6 (Intelligent Imaging Solutions, Edmonton, Alberta).

Flow Cytometry

Cells were dissociated using methods listed above for normal dissociation for each cell type, washed with sterile DPBS and pelleted at 200 g for 4 minutes. Cells were resuspended in 0.5 mL of Flow Cytometry Fixation Buffer (R&D Systems, Minneapolis MN) and incubated at room temperature for 15 minutes. Following fixation cells were washed twice with DPBS, pelleted and resuspended in 200 µL of Flow Cytometry Permeabilisation/Wash Buffer I (R&D Systems, Minneapolis, MN). Primary antibodies (Table 2), were incubated with fixed cells for one hour at 4° C. Cells were then washed and incubated with secondary antibodies for 30 minutes at 4° C. if needed. If included, LipidTox Green/Red Dyes were added at 1:200 dilution in DPBS for 30 minutes after secondary antibody addition. Analysis was performed on a Beckman Coulter CyAn and the results analysed and plotted using FlowJo v10.

Seahorse Extracellular Flux Analysis

Paraxial Mesoderm, BA and white adipocyte (WA) cells were plated on Seahorse XFe24 cell culture microplates (Agilent, Santa Clara, CA) under their normal culture conditions. Briefly, PM cells were plated at a density of 120, 000/cm$^2$ in PMM2 medium supplemented with Y-27632 dihydrochloride (Tocris, Minneapolis, MN) for 24 hours, then switched to PMM2 alone for an additional 48 hours prior to flux analysis. Brown adipocytes were plated as reaggregates at a density of 15 aggregates/cm$^2$ and cultured for 21 days in BAD2. For white adipocyte flux analysis, hADSCs were plated at a density of 10,000 cells/cm$^2$ in MesenPRO™ RS (ThermoFisher, Waltham, MA) medium for four days and then switched to StemPRO® Adipogenesis Differentiation Medium (ThermoFisher, Waltham, MA) for 21 days. For BA cells, media was changed every other day. For the hADSCs fresh MesenPRO was added on the initial day of plating and not changed. During WA differentiation, StemPRO® Adipogenesis Differentiation Medium was changed every three days.

The Mito Stress Test Kit (Agilent, Santa Clara, CA) was utilised to analyse mitochondrial function. The drugs, oligomycin, FCCP and rotenone/antimycin A were titrated for maximal effect against brown adipocytes prior to establishing the flux analysis protocols for the PM and WA cells. Drug concentrations were unchanged throughout all extracellular flux assays: oligomycin was used at 2 µM, FCCP, at 2 µM, and rotenone/antimycin A used at 5 µM.

For the norepinephrine stimulation analysis, the cells were kept in their respective differentiation media until immediately before the assay. For the isoproterenol stimulation assays the PM cells were given PMM2 medium without forskolin and with 100 µM isoproterenol 18 hours prior to the assay. The BA cells were given BAD2 medium without IBMX and with 100 µM isoproterenol for 18 hours prior to the assay. Because the white adipocytes were differentiated in a serum based medium, we sought to normalise any effects from serum on the BA cells by exposing both cells to the same medium for 48 hours for the forskolin stimulation assays. Both the BA and WA cells were given a minimal medium composed of DMEM/F-12 without glutamine (Corning, Corning, NY), 2% ESC-qualified FBS (Atlanta Biological, Flowery Branch, GA), 2 mM Glutagro™ (Corning, Corning, NY), 1× MEM non-essential amino acids (Corning, Corning, NY), 200 ng/mL LONG® R3 IGF-I (Sigma-Aldrich, St. Louis, MO), and 1 µM Dexamethasone (Tocris, Minneapolis, Minn.). Twenty-four hours prior to the assay, this minimal medium was supplemented with 10 µM forskolin. For the fatty acid oxidation assay, both BA and WA cells were given a substrate-limited medium for 24 hours prior to the flux assay. This substrate-limited medium was composed of DMEM without glucose, glutamine or sodium pyruvate (Corning, Corning, NY) supplemented with 0.5 mM glucose (Corning, Corning, NY), 1 mM Glutagro™ (Corning, Corning, NY), 0.5 mM carnitine (Sigma-Aldrich, St. Louis, MO), and 2% ESC-qualified FBS (Atlanta Biological, Flowery Branch, GA).

Prior to the assay, the cells were given freshly prepared XF assay medium. This medium was composed of XF base medium (Agilent, Santa Clara, CA) and desired concentrations of substrates: glucose, glutamine and sodium pyruvate. For the stimulation assays, XF assay medium contained base medium supplemented with 25 mM glucose (Corning, Corning, NY), 2 mM Glutagro™ (Corning, Corning, NY) and 1 mM sodium pyruvate. The medium was warmed to 37° C. and the pH adjusted to 7.4 using sodium hydroxide and filtered through a 0.2 µm Stericup® filter (Millipore, Billerica, MA). At least one hour prior to the start of a flux assay, the growth medium was removed from the XF24 plate and the cells washed three times per manufacturer's protocol with XF assay medium and cells placed in a non-$CO_2$ incubator at 37° C. All drugs utilised during the flux analysis were also diluted from stocks into XF assay medium prior to loading into the assay cartridge ports. For the fatty acid oxidation assays, XF assay medium contained XF base medium supplemented with 5.5 mM glucose and 0.5 mM carnitine.

The 1.5 mM conjugated palmitate-BSA solution was prepared sequentially in a two-step process. First a 1 mM sodium palmitate (Sigma-Aldrich, St. Louis, MO) in 150 mM NaCl solution was made followed by 0.34 mM Fatty Acid Free BSA (Santa Cruz Biotechnology, Dallas, TX) in 150 mM NaCl solution. The sodium palmitate solution was heated to from 37° C. to 70° C. in a water bath on heated stir plate until the solution was clear. Meanwhile, the BSA solution was heated in a water bath on a heated stir plate at 37° C. until it completely dissolved and then sterile filtered with a 0.2 µm Stericup® filter (Millipore, Billerica, MA). Once filtered, the BSA solution was transferred to conical tubes and kept in a 37° C. water bath until ready to mix. For the BSA only control, half of the 0.34 mM BSA NaCl solution was further diluted with an equal volume of 150 mM NaCl solution for a final concentration of 0.17 mM BSA. This solution was aliquoted and stored at −20° C. To complete the palmitate conjugation, an equal volume of hot palmitate was added in 5 mL increments to the remainder of the warm 0.34 mM BSA solution (molar ratio between palmitate and BSA=6:1). This solution was stirred at 37° C. for one hour. The pH was adjusted to 7.4 and the final solution aliquoted into 4 mL glass vials and stored at −20° C.

Following flux analysis, cells were lysed and protein content measured by Bradford assay. Briefly, at the completion of the flux assay, the plate was removed, medium aspirated and the wells rinse gently with ice cold DPBS. The wash was aspirated and the plate was then placed in liquid nitrogen gas phase while fresh lysis buffer was prepared. Lysis buffer was composed of 10 mM Tris, pH 7.4 with 0.1% Triton X-100. The frozen plate was removed and room temperature lysis buffer immediately added. The freezing and addition of relatively warm lysis buffer assisted the lysing of the adipocytes. To the lysed cells, 450 µL of Bradford reagent (Bio-Rad, Hercules, CA) was added to each well. Protein concentration was determined using 100 µL of the lysed cell-Bradford reagent admix at 595 nm on a Biotek Synergy 2. Flux data was the processed via Wave software (Agilent, Santa Clara, CA) and standardised to protein content.

Lipolysis

Human pluripotent stem cells (PSCs), brown adipose (BA) cells and multipotent human adipose-derived stromal/stem cells (hADSCs) were plated in 12-well falcon plates (Fisher Scientific, Hampton, NH). Human PSCs were seeded at 50,000 cells/$cm^2$ and cultured for four days until confluent in MM. Human ADSCs were seeded at 10,000 cells/$cm^2$ and cultured first in MesenPRO™ RS (ThermoFisher, Waltham, MA) for four days until confluent. The medium was then switched to StemPRO® Adipogenesis Differentiation Medium (ThermoFisher, Waltham, MA) for 21 days. Brown adipocyte aggregates were plated in 12-well falcon plates (Fisher Scientific, Hampton, NH) at 15 aggregates/$cm^2$ and cultured for 21 days in BAD2 medium. Lipolysis was measured by glycerol release into the cell culture medium using Free Glycerol Reagent (Sigma Aldrich, St. Louis, MO) according to the manufacturer's instructions. Prior to the assay, the growth medium from each cell type was removed and the cells washed with lipolysis base medium [DMEM (Corning, Corning, NY) supplemented with 2% FA-free BSA (Santa Cruz Biotechnology, Dallas, TX) three times to remove any residual fatty acids from the wells. Lipolysis was stimulated by addition of 10 µM Forskolin (Tocris, Minneapolis, MN) to lipolysis base medium at time "0" with sampling at 4 hour and 8 hour time points. Triacsin C (5 µM) was added to the base medium to inhibit acyl-CoA synthetases and subsequent re-esterfication of glycerol and released fatty acids. Lipolysis data were normalised to protein content.

TABLE 1

Comprehensive List of Antibodies and Dyes

| Primary Antibody/Dye | Application | Dilution/Concentration | Vendor | Catalogue Number |
|---|---|---|---|---|
| CD29-APC | Flow | 20 uL/1 × 10$^6$ cells | BD Pharmingen | 559883 |
| CD34-PE | Flow | 20 uL/1 × 10$^6$ cells | BD Pharmingen | 348057 |
| PDGFRa-PE | Flow | 20 uL/1 × 10$^6$ cells | BD Pharmingen | 556002 |
| CDK2 | WB | 1:2000 | Santa Cruz Biotechnology | sc-163 |
| OCT3/4 | IF | 1:200 | Santa Cruz Biotechnology | sc-8628 |
| SOX2 | IF | 1:200 | Santa Cruz Biotechnology | sc-17320 |
| FOXC1 | Flow/IF | 1:50 (Flow); 1:500 (IF) | Millipore | ABD71 |
| MYF5 | Flow/IF | 0.5 μg/10$^6$ cells (Flow); 1:50 (IF) | R&D Systems | AF4027 |
| MYF5 | WB | 1:1000 | Santa Cruz Biotechnology | sc-302 |
| PAX3 | Flow/IF | 0.25 ug/10$^6$ cells; 5 μg/mL (IF) | R&D Systems | MAB2457 |
| UCP1 | IF | 1:500 | Abcam | ab10983 |
| UCP1-PE | Flow | 10 uL/10$^6$ cells | R&D Systems | IC6158P |
| LipidTox Green | IF | 1:200 | ThermoFisher | H34475 |
| LipidTox Red | Flow | 1:200 | ThermoFisher | H34477 |
| MitoTracker Deep Red | IF | 200 nM | ThermoFisher | M22426 |
| TCOF1/Treacle | WB | 1:1500 | proteintech | 110003-1-AP |
| HNK1 | Flow/IF | 0.2 uL/10$^6$ cells (Flow); 1:300 (IF) | Sigma | C6608 |
| P75 | Flow/IF | 0.2 uL/10$^6$ cells (Flow); 1:100 (IF) | Advanced Targeting Systems | ABN07 |
| AP2 | IF | 1:50 | DSHB | 3B5 |

Example 2—Human iPSC-BA Implant in Mice

Two groups of mice were implanted with human brown adipocytes (hiPSC derived BA cells) produced by the methods of the present invention and encapsulated in a device subcutaneously. In one group, the mice were injected with forskolin (FSK) to stimulate the brown adipocytes. In the other group, the mice implanted with brown adipocytes were not stimulated by FSK. A control group of mice was implanted with an empty device. All groups were assessed after three weeks post-implantation for in vivo PET-SCAN imaging as well as ex vivo PET-SCAN imaging of the explanted device. The group which were implanted with brown adipocytes stimulated by FSK showed an increased signal of labelled glucose than the group implanted with brown adipocytes not stimulated by FSK as analysed by PET-SCAN imaging ex vivo. The mice implanted with empty devices showed no signal.

Calorimetric analyses were performed on group of mice implanted with encapsulated human brown adipocytes or empty devices. One group of mice was depleted of endogenous murine BA tissue by surgery and another group was maintained at thermoneutrality for inactivation of the endogenous murine BA tissue. The two groups were implanted with either human BA cells (hiPSC derived brown adipocytes) or empty devices. After one week post-implantation, each group of mice was stimulated with Norepinephrine (NE) (BA stimulation) to assess uncoupled respiration increase. The four sub-groups were analysed for calorimetry measurements as a readout of the respiration index induced by human brown adipocytes. In the mice surgically depleted from endogenous murine BA cells, NE induced a significant increased respiration index as compared to the mice implanted with empty devices. In the group of mice treated at thermoneutrality, the NE-dependent induction of respiration index was slightly but not significantly improved in the group of mice implanted with human BA cells as compared to the group implanted with empty devices.

All publications mentioned in the above specification are herein incorporated by reference. Various modifications and variations of the disclosed populations of cells, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for in vitro differentiation of human induced pluripotent stem (hIPSC) cells into a population of brown adipocytes, the method comprising culturing the hIPSC cells for about 1-15 days with a transforming growth factor beta (TGF-β) inhibitor to obtain a first population of cells, and then culturing the first population of cells for about 20-50 days in the absence of the TGF-β inhibitor to obtain a second population of cells; and then culturing the second population of cells to form aggregated brown adipocytes.

2. The method of claim 1, wherein the TGF-β inhibitor is a SMAD2 and SMAD3 inhibitor and/or an activin inhibitor.

3. The method of claim 1, wherein the TGF-β inhibitor is:

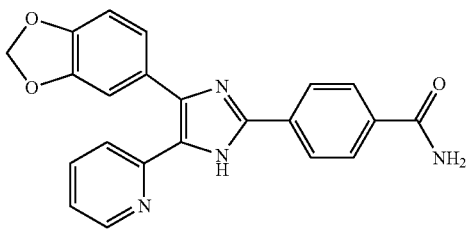 [SMILES: NC(=O)c1ccc(-c2nc(-c3ccc4c(c3)OCO4)c(-c3ccccn3)[nH]2)cc1]

or a salt thereof.

4. The method of claim 1, wherein the hIPSC cells contacted with the TGF-β inhibitor comprise mesoderm cells.

5. The method of claim 4, wherein the mesoderm cells comprise paraxial mesoderm cells.

6. The method of claim 1, wherein the hIPSC cells contacted with the TGF-β inhibitor express FOXC1, FOXC2, MRF4, MSGN1, MYF5, PAX3, PAX7, PRRX1, SIX1 and/or TBX6.

7. The method of claim 1, wherein the hIPSC cells contacted with the TGF-β inhibitor are produced from a population of stem cells using three-dimensional (3D) cell culture.

8. The method of claim 1, wherein the culturing of the hIPSC cells with the TGF-inhibitor is performed for 6-10 days; and the culturing the first population of cells in the absence of the TGF-β inhibitor is performed for 20-30 days.

9. The method of claim 8, wherein the culturing of the hIPSC cells with the TGF-β inhibitor and the culturing the first population of cells in the absence of the TGF-β inhibitor are performed in adherent cultures.

10. The method of claim 8, wherein the culturing the second population of cells to form aggregated brown adipocytes is performed in a rotational suspension culture.

* * * * *